US008227450B2

(12) United States Patent
Milot et al.

(10) Patent No.: US 8,227,450 B2
(45) Date of Patent: Jul. 24, 2012

(54) LYSINE-BASED PRODRUGS OF ASPARTYL PROTEASE INHIBITORS AND PROCESSES FOR THEIR PREPARATION

(75) Inventors: Guy Milot, Longeuil (CA); Stephane Branchaud, Montreal (CA); Brent R. Stranix, Pointe-Claire (CA)

(73) Assignee: Ambrilia Biopharma Inc., Verdun, QC (CA)

( * ) Notice: Subject to any disclaimer, the term of this patent is extended or adjusted under 35 U.S.C. 154(b) by 484 days.

(21) Appl. No.: 12/086,184

(22) PCT Filed: Nov. 30, 2006

(86) PCT No.: PCT/CA2006/001963
§ 371 (c)(1),
(2), (4) Date: Jan. 28, 2010

(87) PCT Pub. No.: WO2007/062526
PCT Pub. Date: Jun. 7, 2007

(65) Prior Publication Data
US 2010/0130765 A1       May 27, 2010

Related U.S. Application Data

(60) Provisional application No. 60/740,642, filed on Nov. 30, 2005.

(51) Int. Cl.
*A61K 31/661*      (2006.01)
*C07F 9/09*        (2006.01)
(52) U.S. Cl. ............................... 514/143; 562/15; 562/36
(58) Field of Classification Search ...................... None
See application file for complete search history.

(56) References Cited

U.S. PATENT DOCUMENTS

| | | | |
|---|---|---|---|
| 5,013,861 A | 5/1991 | Weller, III et al. |
| 5,527,829 A | 6/1996 | Kalish |
| 5,614,522 A | 3/1997 | Talley et al. |
| 5,714,605 A | 2/1998 | Vazquez et al. |
| 5,776,718 A | 7/1998 | Palmer et al. |
| 5,965,588 A | 10/1999 | Vazquez et al. |
| 5,985,870 A | 11/1999 | Getman et al. |
| 6,022,994 A | 2/2000 | Vazquez et al. |
| 6,127,372 A | 10/2000 | Tung et al. |
| 6,159,995 A | 12/2000 | Thorwart et al. |
| 6,384,036 B1 | 5/2002 | Freskos et al. |
| 6,436,989 B1 | 8/2002 | Hale et al. |
| 6,455,587 B1 | 9/2002 | Bouzide et al. |
| 6,506,786 B2 | 1/2003 | Stranix et al. |
| 6,528,532 B1 | 3/2003 | Stranix et al. |
| 6,608,100 B1 | 8/2003 | Stranix et al. |
| 6,610,689 B2 | 8/2003 | Stranix et al. |
| 6,632,816 B1 | 10/2003 | Stranix et al. |
| 6,656,965 B2 | 12/2003 | Stranix et al. |
| 6,677,367 B2 | 1/2004 | Stranix et al. |
| 6,703,403 B2 | 3/2004 | Norbeck et al. |
| 7,388,008 B2 * | 6/2008 | Stranix et al. ............ 514/237.5 |
| 8,008,297 B2 | 8/2011 | Stranix et al. |
| 2006/0025592 A1 | 2/2006 | Stranix et al. |
| 2006/0287316 A1 | 12/2006 | Wu et al. |
| 2009/0253926 A1 | 10/2009 | Milot et al. |
| 2010/0184974 A1 | 7/2010 | Stranix et al. |

FOREIGN PATENT DOCUMENTS

| | | |
|---|---|---|
| CA | 2 089 747 | 4/1992 |
| CA | 2 077 948 | 3/1993 |
| CA | 2 316 218 | 7/1999 |
| EP | 0 532 466 | 3/1993 |
| EP | 0 763 017 | 3/1997 |
| JP | 6321950 | 11/1994 |
| WO | WO 92/06998 | 4/1992 |
| WO | WO 95/06998 | 3/1995 |
| WO | WO 65/24385 | 9/1995 |
| WO | WO 97/27180 | 7/1997 |
| WO | WO 98/31664 | 7/1998 |
| WO | WO 99/33815 | 7/1999 |
| WO | WO 99/55687 | 11/1999 |
| WO | WO 00/47551 | 8/2000 |
| WO | WO 00/76961 | 12/2000 |
| WO | WO 01/68593 | 9/2001 |
| WO | WO 02/64551 | 8/2002 |
| WO | WO 03/74467 | 9/2003 |
| WO | WO 2004/054586 | 7/2004 |

(Continued)

OTHER PUBLICATIONS

Anderson et al., "The use of Esters of N-Hydroxysuccinimide in Peptide Synthesis," *J. Am. Chem. Soc.* 86(9):1839-1842 (1964).
Andrade et al., "HIV-Related Drug Metabolism and Cytochrome P450 Enzymes," *AIDS Clin. Care* 12(11):91-95 (2000).
Bouzide et al., "Lysine Derivatives as Potent HIV Protease Inhibitors. Discovery, Synthesis and Structure-Activity Relationship Studies," *Bioorg. Med. Chem. Lett.* 15:1509-1513 (2005).
Boyle et al., "Asymmetric Transformation of α-Amino-ε-Caprolactam, A Lysine Precursor," *J. Org. Chem.* 44(26):4841-4847 (1979).
Bukrinsky et al., "Active Nuclear Import of Human Immunodeficiency Virus Type 1 Preintegration Complexes," *Proc. Natl. Acad. Sci. USA* 89(14):6580-6584 (1992).

(Continued)

*Primary Examiner* — Yong Chu
*Assistant Examiner* — Michael Barker
(74) *Attorney, Agent, or Firm* — Clark & Elbing LLP

(57) ABSTRACT

The present invention provides processes for synthesizing lysine based compounds of the formula;

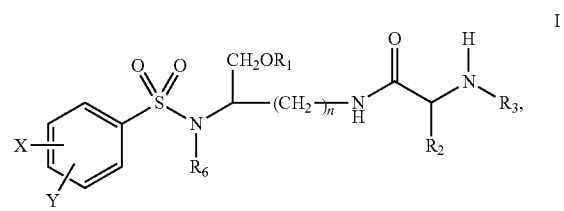

wherein $R_1$ may be, for example, $(HO)_2P(O)-$, $(NaO)_2P(O)-$, wherein X may be, for example, $NH_2$, Y may be H, F, Cl, or Br, and wherein n, X', Y', $R_2$, $R_3$, $R_4$, $R_5$ and $R_6$ are as defined herein.

21 Claims, 2 Drawing Sheets

FOREIGN PATENT DOCUMENTS

| | | |
|---|---|---|
| WO | WO 2004/056764 | 7/2004 |
| WO | WO 2005/066131 | 7/2005 |
| WO | WO 2006/012725 | 2/2006 |
| WO | WO 2006/114001 | 11/2006 |
| WO | WO 2006114001 A1 * | 11/2006 |
| WO | WO 2007/062526 | 6/2007 |
| WO | WO 2008/023273 | 2/2008 |
| WO | WO 2008/078200 | 7/2008 |

OTHER PUBLICATIONS

Calogeropoulou et al., "Strategies in the Design of Prodrugs of Anti-HIV Agents, in Particular in Regards to Pro-Drugs of Nucleoside Transcriptase Inhibitors and Prodrugs of Protease Inhibitors," *Current Topics in Medicinal Chemistry* 3: 1467-1495 (2003).
Chemical Abstracts, 123(7), Abstract 83099w (1995), Harada and Mikio.
Chemical Abstracts, 46(13), Abstract 6593c (1952), Izumiya.
Chemical Abstracts, 46(13), Abstract 6593g (1952), Izumiya.
Chemical Abstracts, 46(13), Abstract 6593i (1952), Izumiya.
Chemical Abstracts, 62(2), Abstract 1740c (1965), Hermann, et al.
Chong et al., "Peptidomimetic HIV Protease Inhibitors: Phosphate Prodrugs with Improved Biological Acitivities," *J. Med. Chem.* 36(17):2575-2577, 1993.
Dandache et al., "In Vitro Antiviral Activity and Cross-Resistance Profile of PL-100, a Novel Protease Inhibitor of Human Immunodeficiency Virus Type 1," *Antimicrob. Agents Chemother.* 51(11):4036-4043 (2007).
Dankwardt et al., "Amino Acid Derived Sulfonamide Hydroxamates as Inhibitors of Procollagen C-Proteinase. Part 2: Solid-Phase Optimization of Side Chains," *Bioorg. Med. Chem. Lett.* 12:1233-1235 (2002).
El-Naggar et al., "Synthesis and Biological Activity of Some New Quinoline-8-Sulphonylamino Acid and Dipeptide Derivatives,"*Acta Pharm. Jugosl.*, 33(2):103-110 (1983), XP000926585.
El-Naggar et al., "Synthesis of Nitrobenzene- and Nitrotoluenesulfonylamino Acid and Dipeptide Derivatives," *Pol. J. Chem.*, 52(3):637-642 (1978), XP000926586.
Elmore et al., "Kinetics and Mechanism of Catalysis by Proteolytic Enzymes," *Biochem. J.*, 102:728-734 (1967).
Ettmayer et al., "Lessons Learned from Marketed and Investigational Prodrugs," *J. Med. Chem.*, 47(10):2393-2404 (2004).
Fitzsimmons et al., "Selective Biotransformation of the Human Immunodeficiency Virus Protease Inhibitor Saquinavir by Human Small-Intestinal Cytochrome P4503A4," *Drug Metab. Disp.*, 25(2):256-266 (1997).
Gallay et al., "HIV-1 Infection of Nondividing Cells: C-Terminal Tyrosine Phosphorylation of the Viral Matrix Protein is a Key Regulator," *Cell*, 80(3):379-388 (1995).
Garrity et al., "A New Synthetic Route to 2-(p-Nitrobenzyl)-1,4,7,10-Tetraazacyclododecane," *Tetrahedron Letters*, 34(35):5531-5534 (1993).
Goff, "Retroviral Reverse Transcriptase: Synthesis, Structure, and Function," *Journal of Acquired Immune Deficiency Syndromes*, 3(8):817-831(1990).
Greene and Wuts, "Protection for the Amino Group," *Protective Groups in Organic Synthesis*, 3$^{rd}$ Ed., 518-525 (John Wiley & Sons, Inc., 1999).
Greene, "Protection for the Amino Group," *Protective Groups in Organic Synthesis*, 258-263 (John Wiley & Sons, Inc., 1981).
Hamill et al., Non-Peptide Fibrinogen Receptor Antagonists. Synthesis of [$^3$H]L-756,568, *J. Labelled Cpd. Radiopharm.*, 42(6):605-609 (1999), XP000926587.
Haseltine, "Molecular Biology of the Human Immunodeficiency Virus Type 1," *The FASEB Journal*, 5(10):2349-2360 (1991).
Hlavacek et al., "An Alternative Route to N$^\alpha$-methylamino Acid Derivatives: Synthesis and Conformation of Some N$^\alpha$-acetyl-N$^\alpha$-methylamino Acid Methylamides," *Collection Czech. Chem. Commun.*, 53:2473-2494 (1988), XP001002995.
Japour et al., "Standardized Peripheral Blood Mononuclear Cell Culture Assay for Determination of Drug Susceptibilities of Clinical Human Immunodeficiency Virus Type 1 Isolates," *Antimicrobial Agents and Chemotherapy*, 37(5):1095-1101 (1993).
Karup et al., "9-Acridinylpeptides and 9-Acridinyl-4-Nitrophenylsulfonylpeptides," *Int. J. Peptide Protein Res.*, 32(5):331-343 (1988), XP000926584.
Kempf et al., "Pharmacokinetic Enhancement of Inhibitors of the Human Immunodeficiency Virus Protease by Coadministration with Ritonavir," *Antimicrob. Agents Chemother.*, 41(3):654-660 (1997).
Kolc, "Amino Acids and Peptides," *Collect. Czech. Chem. Commun.*, 34(2):630-634 (1969).
Kottirsch et al., "Beta-Amino Acid Derivatives as Orally Active Non-Peptide Fibrinogen Receptor Antagonists," *Bioorg. Med. Chem. Lett.*, 7(6):727-732 (1997), XP004136118.
Lasky et al., "Delineation of a Region of the Human Immunodeficiency Virus Type 1 gp120 Glycoprotein Critical for Interaction with the CD4 Receptor," *Cell*, 50(6):975-985 (1987).
Leclerc et al., "On the Selectivity of Acylation of Unprotected Diamino Acids," *Can. J. Chem.*, 46(7):1047-1051 (1968), XP000926722.
Lescrinier et al., "α-Amino Acids Derived From Ornithine as Building Blocks for Peptide Synthesis," *J. Peptide Res.*, 49(2):183-189 (1997), XP000679594.
Maeda et al., "Amino Acids and Peptides. V. Synthesis of Amino Acid Derivatives Containing a Sulfonamide Bond," *Chem. Pharm. Bull.*, 33(5):2137-2141 (1985), XP001010687.
Matayoshi et al., "Novel Fluorogenic Substrates for Assaying Retroviral Proteases by Resonance Energy Transfer," *Science*, 247(4945):954-958 (1990).
Meek et al., "Inhibition of HIV-1 Protease in Infected T-Lymphocytes by Synthetic Peptide Analogues," *Nature*, 343(6253):90-92 (1990).
Pauwels et al., "Rapid and Automated Tetrazolium-Based Colorimetric Assay for the Detection of Anti-HIV Compounds," *J. Virological Methods*, 20(4):309-321 (1988).
Poduska et al., "Amino Acids and Peptides. L11. Intramolecular Aminolysis of Amide Bonds in Derivatives of α,γ-Diaminobutyric acid, α,γ-Diaminopropionic Acid, and Ornithine," *Coll. Czech. Chem. Commun.*, 30(7):2410-2433 (1965).
Sakai et al., "Integration is Essential for Efficient Gene Expression of Human Immunodeficiency Virus Type 1," *J. Virol.*, 67(3):1169-1174 (1993).
Schon et al., "9-Fluorenylmethyl Pentafluorophenyl Carbonate as a Useful Reagent for the Preparation of N-9-Fluorenylmethyloxycarbonylamino Acids and Their Pentafluorophenyl Esters," *J. of Synthetic Org. Chem.*, 4:303-305 (1986), XP002182716.
Sevigny et al., "Antiviral Activity and Cross-Resistance Profile of P-1946, A Novel Human Immunodeficiency Virus Type 1 Protease Inhibitor," *Antiviral Res.* 70(2):17-20 (2006).
Sohma et al., "Development of Water-Soluble Prodrugs of the HIV-1 Protease Inhibitor KNI-727: Importance of the Conversion Time for Higher Gastrointestinal Absorption of Prodrugs Based on Spontaneous Chemical Cleavage," *J. Med. Chem.* 46(19):4124-4135, 2003.
Solinas et al., "The Oxidative Deamination of I-Aminoethylcysteine Sulfoxide and Sulfone by Snake Venom I-Amino Acid Oxidase," *Physiol. Chem. Phys. Med. NMR*, 25(4):281-285 (1993).
Stranix et al., "Lysine Sulfonamides as Novel HIV-Protease Inhibitors: Optimization of the Nepsilon-Acyl-Phenyl Spacer,"*Bioorg Med Chem Lett.* 13(24):4289-4292 (2003).
Stranix et al., "Lysine Sulfonamides as Novel HIV-Protease Inhibitors: Nepsilon-Disubstituted Ureas," *Bioorg Med Chem Lett.* 14(15):3971-3974 (2004).
Stranix et al., "Lysine Sulfonamides as Novel HIV-Protease Inhibitors: Nepsilon-Acyl Aromatic Alpha-Amino Acids," *Bioorg Med Chem Lett.* 16(13):3459-3462 (2006).
Treluyer et al., "Oxidative Metabolism of Amprenavir in the Human Liver. Effect of the CYP3A Maturation," *Drug Metab. Disp.* 31(3):275-281 (2003).
Vierling et al., "Prodrugs of HI Protease Inhibitors," *Current Pharmaceutical Design*. 9: 1755-1770 (2003).
International Search Report for PCT/CA2001/00296, dated Nov. 27, 2001, mailed Dec. 10, 2001.
International Search Report for PCT/CA2004/001440, mailed Dec. 10, 2004.
Written Opinion for PCT/CA2004/001440, mailed Dec. 10, 2004.
European Search Report for EP 08021798.7 dated May 12, 2010.
European Examination Report for EP 08021798.7 dated May 25, 2010.

\* cited by examiner

LYSINE-BASED PRODRUGS OF ASPARTYL PROTEASE INHIBITORS AND PROCESSES FOR THEIR PREPARATION

CROSS-REFERENCE TO RELATED APPLICATIONS

This application is the U.S. national stage filing under 35 U.S.C. §371 of International Application No. PCT/CA2006/001963, filed Nov. 30, 2006, which claims benefit of U.S. Provisional Patent Application No. 60/740,642, filed Nov. 30, 2005, each of which is hereby incorporated by reference.

TECHNICAL FIELD OF THE INVENTION

The present invention relates to a process for synthesizing compounds which are used for impairing human immunodeficiency virus (HIV) replication. More particularly, the present invention relates to a process for synthesizing a lysine based compound which is able to release an active HIV protease inhibitor upon cleavage of a physiologically cleavable unit. The invention also relates to intermediates useful for the synthesis of these compounds.

BACKGROUND OF THE INVENTION

Inhibitors of the HIV viral protease have been developed relatively recently and their use began only in 1996. Currently, they are considered the most effective drugs against HIV infection. Unfortunately, most current proteases inhibitors are relatively large hydrophobic molecules that possess rather low bioavailability. A high pill burden is therefore required to attain the therapeutic dose in a patient. This is a deterrent, which too often results in patient non-compliance and inadequate treatment results. This situation leads to sub-optimal therapeutic drug concentration that in turns leads to the development of HIV resistant strains. Consequently, there is an urgent need to improve the solubility and bioavailability of proteases inhibitors.

Protease inhibitors have also been developed in the form of prodrugs such as those described, for example, in U.S. Pat. No. 6,436,989 to Hale et al, the entire content of which is incorporated herein by reference. These prodrugs possess favourable aqueous solubility, high oral bioavailability and allow the in vivo generation of the active ingredient. However, it is well known that HIV has the ability to develop resistance to the currently available drugs. A need remains for alternative HIV protease inhibitors active towards wild-type and resistant viral strains and which shows enhanced solubility and bioavailability.

The synthesis of a unique class of aromatic derivatives which are inhibitors of aspartyl proteases is described in U.S. Pat. No. 6,632,816 to Stranix et al, the entire content of which is incorporated herein by reference. This patent includes, more particularly, N-synthetic amino acid substituted L-lysine derivatives possessing potent aspartyl protease inhibitory properties. Lysine based compounds demonstrating enhanced aqueous solubility and bioavailability as well as their method of preparation have also been described in U.S. application Ser. No. 09/902,935 (Stranix et al.) published Feb. 2, 2006 under publication No. US2006/0025592A1.

Efficient and improved route of synthesizing these compounds are needed in order to develop commercially-viable processes. A desirable route of synthesis should produce the compounds in a good yield, with the minimum number of step possible and in a manner that is of minimum impact to the environment in terms of disposing of waste-materials. Intermediate compounds are also of help in facilitating the synthesis of end compounds. There thus remains a need for optimizing synthesis of lysine based compounds.

The present invention seeks to meet these and other needs.

SUMMARY OF THE INVENTION

Novel lysine based compounds originating from a class of derivatives that are potent aspartyl protease inhibitors, pharmaceutically acceptable derivatives and pharmaceutical compositions are illustrated herein and have been described in U.S. publication No. US2006/0025592A1. These lysine based compounds have a cleavable unit which may readily be cleaved in vivo to release an active ingredient which has an affinity for HIV aspartyl protease (U.S. Pat. No. 6,632,816) and which are active for inhibiting (impairing) HIV replication. The compounds described herein may have, for example, a (e.g., physiologically, enzymatically) cleavable (e.g., hydrolysable) bond or unit which upon cleavage of the cleavable bond or unit generates a protease inhibitor (e.g., an active protease inhibitor).

The present invention provides in one aspect thereof, efficient processes or methods for synthesizing the lysine based compounds described herein including their derivatives and pharmaceutically acceptable salts.

In accordance with the present invention, processes for synthesizing a lysine based compound using any one of the relevant compounds disclosed in U.S. Pat. No. 6,632,816 to Stranix et al. as starting material are encompassed herewith. Further in accordance with the present invention, processes for synthesizing compounds able to generate any one of the compound disclosed in U.S. Pat. No. 6,632,816 to Stranix et al. upon cleavage of a (in vivo) cleavable unit are also encompassed herewith.

More particularly, the present invention in accordance with one aspect thereof, provides a process for synthesizing a compound (e.g. a compound able to generate an HIV protease inhibitor) of formula I:

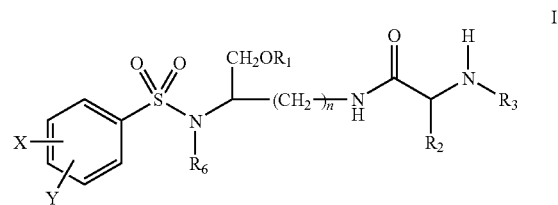

pharmaceutically acceptable salts and derivatives thereof (e.g., for example, when the compound of the present invention comprises an amino group, the pharmaceutically acceptable salt may be an ammonium salt),
wherein n may be, for example, 3 or 4,
wherein X and Y, the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_4R_5$, —NH-$COR_4$, —$OR_4$, —$COOR_4$, —$COR_4$, and —$CH_2OH$ or X and Y together define an alkylenedioxy group selected from the group consisting of a methylenedioxy group of formula —$OCH_2O$— and an ethylenedioxy group of formula —$OCH_2CH_2O$—,
wherein $R_6$ may be selected, for example, from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof,
wherein $R_3$ may be selected, for example, from the group consisting of H, a straight alkyl group of 1 to 6 carbon atoms, a branched alkyl group of 3 to 6 carbon atoms, a cycloalkyl group of 3 to 6 carbon atoms, and a group of formula $R_{3A}$—CO—, wherein $R_{3A}$ may be selected, for example, from the group consisting of a straight or branched alkyl group of 1 to 6 carbon atoms (e.g. methyl, ethyl-, propyl, iso-propyl, butyl, iso-butyl, tert-butyl, tert-butyl-$CH_2$—, etc.), a cycloalkyl group having 3 to 6 carbon atoms (e.g. cyclopropyl-, cyclohexyl- etc.), a cycloalkylalkyl group having 3 to 6 carbon atoms in the cycloalkyl part thereof and 1 to 3 carbon atoms in the alkyl part thereof, (e.g. cyclopropyl-$CH_2$—, cyclohexyl-$CH_2$—, etc.), an alkyloxy group of 1 to 6 carbon atoms (e.g. $CH_3O$—, $CH_3CH_2O$—, iso-butylO-, tert-butylO-(Boc), etc.), tetrahydro-3-furanyloxy, —$CH_2OH$, —$CF_3$, —$CH_2CF_3$, —$CH_2CH_2CF_3$, pyrrolidinyl, piperidinyl, 4-morpholinyl, $CH_3O_2C$—, $CH_3O_2CCH_2$—, Acetyl-$OCH_2CH_2$—, $HO_2CCH_2$—, 3-hydroxyphenyl, 4-hydroxyphenyl, 4-$CH_3OC_6H_4CH_2$—, $CH_3NH$—, $(CH_3)_2N$—, $(CH_3CH_2)_2N$—, $(CH_3CH_2CH_2)_2N$—, $HOCH_2CH_2NH$—, $CH_3OCH_2O$—, $CH_3OCH_2CH_2O$—, $C_6H_5CH_2O$—, 2-pyrrolyl, 2-pyridyl, 3-pyridyl, 4-pyridyl-, 2-pyrazinyl, 2-quinolyl, 3-quinolyl, 4-quinolyl, 1-isoquinolyl, 3-isoquinolyl, 2-quinoxalinyl, a phenyl group of formula

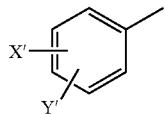

a picolyl group selected from the group consisting of

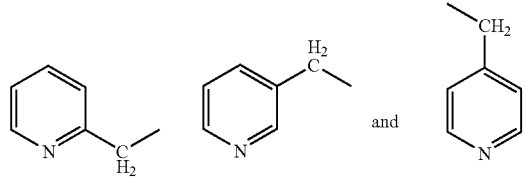

a picolyloxy group selected from the group consisting of

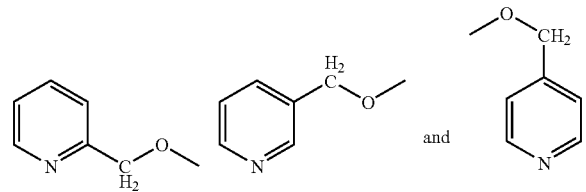

a substituted pyridyl group selected from the group consisting of

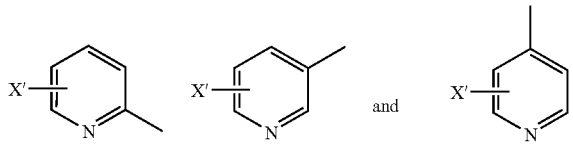

and a group of formula,

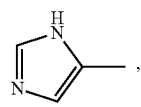

wherein X' and Y', the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_4R_5$, —$NHCOR_4$, —$OR_4$, —$COOR_4$, —$COR_4$ and —$CH_2OH$, wherein $R_4$ and $R_5$, the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, and tert-butoxycarbonyl, wherein $R_2$ may be selected, for example, from the group consisting of a diphenylmethyl group of formula IV

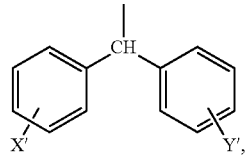

a naphthyl-1-$CH_2$— group of formula V

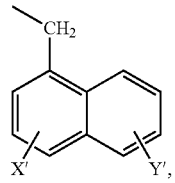

a naphthyl-2-$CH_2$— group of formula VI

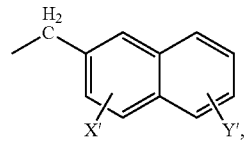

and wherein $R_1$ may be a cleavable unit (e.g., a physiologically cleavable unit), whereby upon cleavage of the unit, the compound releases a protease inhibitor (an HIV protease inhibitor). For example, $R_1$ may be an enzymatically or metabolically cleavable unit or hydrolysable bond which may be cleaved under enteric and/or gastrointestinal conditions (pH) or other physiological conditions.

In accordance with the present invention, $R_1$ may be selected, for example, from the group consisting of $(HO)_2P(O)$ and $(MO)_2P(O)$, wherein M is an alkali metal (e.g. Na, K, Cs, etc) or alkaline earth metal (Ca, Mg, etc.).

$R_1$ may also be an intermediate group able to be transformed into a suitable group useful for the generation of a protease inhibitor or lysine based compound described herein. Further in accordance with the present invention, $R_1$ may therefore be, for example; $(C_1-C_4\ AlkylO)_2P(O)$, etc.

The present invention further provides in another aspect a process for synthesizing a compound of formula II,

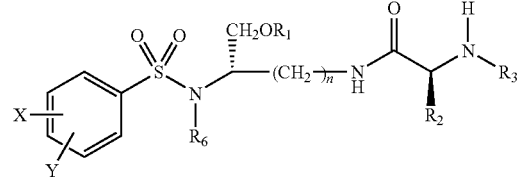

to pharmaceutically acceptable salts and derivatives thereof (e.g., for example, when the compound of the present invention comprises an amino group, the pharmaceutically acceptable salt may be an ammonium salt), wherein n may be 3 or 4, wherein X and Y, the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —CF$_3$, —OCF$_3$, —CN, —NO$_2$, —NR$_4$R$_5$, —NHCOR$_4$, —SR$_4$, —COOR$_4$, —COR$_4$, and —CH$_2$OH or X and Y together define an alkylenedioxy group selected from the group consisting of a methylenedioxy group of formula —OCH$_2$O— and an ethylenedioxy group of formula —OCH$_2$CH$_2$O—, wherein R$_6$ may be selected, for example, from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof, wherein R$_3$ may be selected, for example, from the group consisting of H, a straight alkyl group of 1 to 6 carbon atoms, a branched alkyl group of 3 to 6 carbon atoms, a cycloalkyl group of 3 to 6 carbon atoms, and a group of formula R$_{3A}$—CO—, wherein R$_{3A}$ may be selected, for example, from the group consisting of a straight or branched alkyl group of 1 to 6 carbon atoms (e.g. methyl, ethyl-, propyl, iso-propyl, butyl, iso-butyl, tert-butyl, tert-butyl-CH$_2$—, etc.), a cycloalkyl group having 3 to 6 carbon atoms (e.g. cyclopropyl-, cyclohexyl- etc.), a cycloalkylalkyl group having 3 to 6 carbon atoms in the cycloalkyl part thereof and 1 to 3 carbon atoms in the alkyl part thereof, (e.g. cyclopropyl-CH$_2$—, cyclohexyl-CH$_2$—, etc.), an alkyloxy group of 1 to 6 carbon atoms (e.g. CH$_3$O—, CH$_3$CH$_2$O—, iso-butylO-, tert-butylO-(Boc), etc.), tetrahydro-3-furanyloxy, —CH$_2$OH, —CF$_3$, —CH$_2$CF$_3$, —CH$_2$CH$_2$CF$_3$, pyrrolidinyl, piperidinyl, 4-morpholinyl, CH$_3$O$_2$C—, CH$_3$O$_2$CCH$_2$—, Acetyl-OCH$_2$CH$_2$—, HO$_2$CCH$_2$—, 3-hydroxyphenyl, 4-hydroxyphenyl, 4-CH$_3$OC$_6$H$_4$—CH$_2$—, CH$_3$NH—, (CH$_3$)$_2$N—, (CH$_3$CH$_2$)$_2$N—, (CH$_3$CH$_2$CH$_2$)$_2$N—, HOCH$_2$CH$_2$NH—, CH$_3$OCH$_2$O—, CH$_3$OCH$_2$CH$_2$O—, C$_6$H$_5$CH$_2$O—, 2-pyrrolyl, 2-pyridyl, 3-pyridyl, 4-pyridyl, 2-pyrazinyl, 2-quinolyl, 3-quinolyl, 4-quinolyl, 1-isoquinolyl, 3-isoquinolyl, 2-quinoxalinyl, a phenyl group of formula

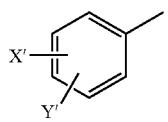

a picolyl group selected from the group consisting of

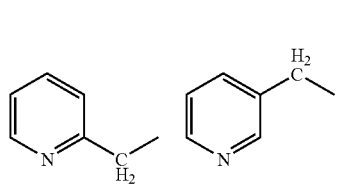 and 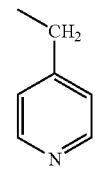

a picolyloxy group selected from the group consisting of

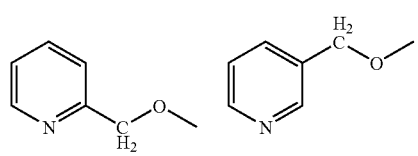 and

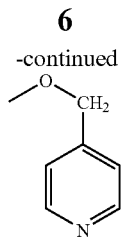

a substituted pyridyl group selected from the group consisting of

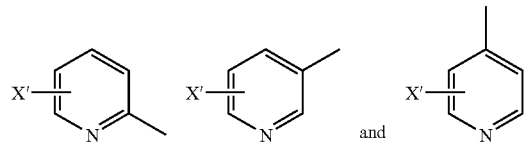

and a group of formula,

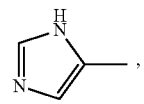

wherein X' and Y', the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —CF$_3$, —NO$_2$, —NR$_4$R$_5$, —NHCOR$_4$, —OR$_4$, —SR$_4$, —COOR$_4$, —COR$_4$ and —CH$_2$OH, wherein R$_4$ and R$_5$, the same or different, may be selected, for example, from the group consisting of H, a straight alkyl group of 1 to 6 carbon atoms, a branched alkyl group of 3 to 6 carbon atoms, and a cycloalkyl group of 3 to 6 carbon atoms, wherein R$_2$ may be selected from the group consisting of a diphenylmethyl group of formula IV

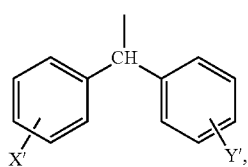

IV a naphthyl-1-CH$_2$— group of formula V

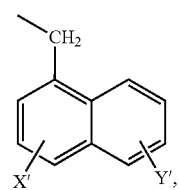

V a naphthyl-2-CH$_2$— group of formula VI

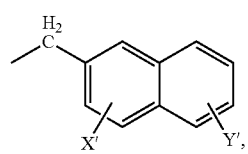

VI and wherein $R_1$ may be a physiologically cleavable unit, whereby upon cleavage of the unit the compound may be able to release a protease inhibitor.

In accordance with the present invention, $R_1$ may, more particularly, be selected, for example, from the group consisting of $(HO)_2P(O)$ and $(MO)_2P(O)$, wherein M is an alkali metal (e.g. Na, K, Cs, etc) or alkaline earth metal (Ca, Mg, etc.).

$R_1$ may also be an intermediate group able to be transformed into a suitable group useful for the generation of a protease inhibitor or lysine based compound described herein. Further in accordance with the present invention, $R_1$ may therefore be, for example; $(C_1-C_4 \text{ Alkyl}O)_2P(O)$, etc.

The present invention therefore provides a process for synthesizing a compound of formula I or formula II described herein wherein n may be, more particularly, 4.

The present invention also provides a process for synthesizing a compound of formula I or formula II described herein where X and Y, the same or different, may be, more specifically selected from the group consisting of methyl, ethyl, H, F, Cl, Br, I and $-NR_4R_5$.

In accordance with the present invention X and Y, the same or different, may be for example, H, For $NH_2$.

In accordance with the present invention $R_4$ and $R_5$, the same or different, may be for example, H.

The present invention also provides a process for synthesizing a compound of formula I or formula H described herein where $R_6$ may be, more particularly, selected from the group consisting of a straight alkyl group of 1 to 6 carbon atoms and a branched alkyl group of 3 to 6 carbon atoms. In accordance with the present invention $R_6$ may be for example, iso-butyl.

The present invention also provides a process for synthesizing a compound of formula I or formula II described herein where $R_3$ may be, more specifically a group of formula $R_{3A}-CO-$, wherein $R_{3A}$ may be selected, for example, from the group consisting of a straight or branched alkyl group of 1 to 6 carbon atoms (e.g. methyl, ethyl-, propyl, iso-propyl, butyl, iso-butyl, tert-butyl, tert-butyl-$CH_2-$, etc.), an alkyloxy group of 1 to 6 carbon atoms. In accordance with the present invention $R_{3A}$ may be, for example, a straight alkyl group of 1 to 6 carbon atoms or even more particularly methyl, ethyl or propyl.

The present invention also provides a process for synthesizing a compound of formula I or formula II described herein where X' and Y', the same or different, may be selected, for example, from the group consisting of H, methyl, ethyl, F, Cl, Br, I and $-NR_4R_5$. More particularly, X' and Y' may be H.

The present invention also provides a process for synthesizing a compound of formula I or formula II described herein where $R_2$ is more particularly a diphenylmethyl group (substituted with X' and/or Y' or unsubstituted).

The present invention also provides a process for synthesizing a compound of formula I or formula II described herein where $R_2$ is more particularly a naphthyl-1-$CH_2-$ group or a naphthyl-2-$CH_2-$ group (substituted with X' and/or Y' or unsubstituted).

The present invention also provides a process for synthesizing a compound of formula I or to formula II described herein where $R_1$ may be, more particularly $(HO)_2P(O)$.

For example, processes for synthesizing the following exemplary compounds, without limitation, are encompassed by the present invention;

a compound of formula I or II wherein n is 4, $R_1$ is $(HO)_2P(O)$, X is $NH_2$, Y is H or F, X' is H, Y' is H, $R_6$ is iso-butyl and $R_3$ is $CH_3O-CO$;

a compound of formula I or II wherein n is 4, $R_1$ is $(HO)_2P(O)$, X is $NH_2$, Y is H or F, X' is H, Y' is H, $R_6$ is iso-butyl and $R_3$ is 4-morpholine-CO;

a compound of formula I or II wherein n is 4, $R_1$ is $(HO)_2P(O)$, X is 4-$NH_2$, Y is H, X' is H, Y' is H, $R_6$ is iso-butyl and $R_3$ is $CH_3O-CO$ and $R_2$ is as described herein;

a compound of formula I or II wherein n is 4, $R_1$ is $(HO)_2P(O)$, X is 4-$NH_2$, Y is H, X' is H, Y' is H, $R_6$ is iso-butyl and $R_3$ is 4-morpholine-CO and $R_2$ is as described herein;

a compound of formula I or II wherein n is 4, $R_1$ is $(HO)_2P(O)$, X is 4-$NH_2$, Y is 3-F, X' is H, Y' is H, $R_6$ is iso-butyl and $R_3$ is $CH_3O-CO$ and $R_2$ is as described herein;

a compound of formula I or II wherein n is 4, $R_1$ is $(HO)_2P(O)$, X is 4-$NH_2$, Y is 3-F, X' is H, Y' is H, $R_6$ is iso-butyl and $R_3$ is 4-morpholine-CO and $R_2$ is as described herein;

a compound of formula I or II wherein n is 4, $R_1$ is $(HO)_2P(O)$, X is 4-$NH_2$, Y is H, X' is H, Y' is H, $R_6$ is iso-butyl and $R_3$ is $CH_3O-CO$ and $R_2$ is a naphthyl-2-$CH_2$, and a compound of formula I or II wherein n is 4, $R_1$ is $(HO)_2P(O)$, X is 4-$NH_2$, Y is H, X' is H, Y' is H, $R_6$ is iso-butyl and $R_3$ is 4-morpholine-CO and $R_2$ is naphthyl-1-$CH_2$.

In an exemplary embodiment of the present invention there is provided a process for synthesizing a compound of formula IIIA:

IIIA the process may comprise a) reacting a compound of formula IA:

IA with a reagent mixture for converting an alcohol functional group of compound IA into a phosphoester functional group and b) converting the phosphoester functional group of the resulting intermediate into a phosphonic acid functional group. In accordance with the present invention, X, Y, X', Y', n, $R_2$, $R_3$, $R_4$, $R_5$ and $R_6$ are as defined herein and may be the same for both the above mentioned formulas.

In accordance with the present invention step a) may be carried out at a temperature ranging from about 0° C. to about 40° C. (e.g., about 0° C. to about 30° C.). Further in accordance with the present invention, step a) may be carried out by dissolving compound IA in a polar aprotic solvent (e.g., tetrahydrofurane, acetonitril, DMF, etc.) and triethyl phosphate followed by the addition of a dialkyl chlorophosphate (e.g., diethyl chlorophosphate) and then metal hydride (e.g., alkali metal hydride, (e.g., sodium hydride)) (about 1.5 equivalent each). Step a) may also comprise extracting and purifying (isolating) the resulting intermediate (compound IIA).

Also in accordance with the present invention step b) may be carried out at a temperature ranging from about 0° C. to about 40° C. (e.g., about 0° C. to about 30° C.). Further in accordance with the present invention, step b) may be carried out by dissolving the intermediate of step a) in a solvent (e.g., anhydrous dichloromethane or any equivalent thereof) and reacting with trimethylsilyl bromide (bromotrimethylsilane), iodotrimethylsilane, HBr or chemical equivalent thereof. Also in accordance with the present invention, step b) may also comprise a step of removing (e.g., by evaporation) the solvent therefore providing compound IIIA.

In another exemplary embodiment, the present invention relates to a process for synthesizing a compound of formula III:

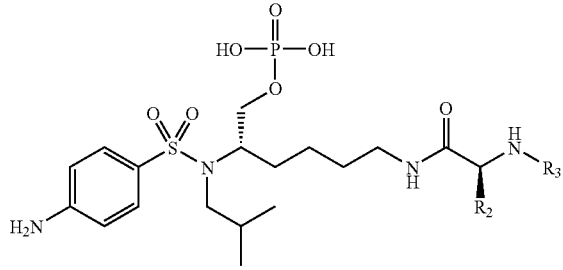

the process may comprise a) reacting a compound of formula I:

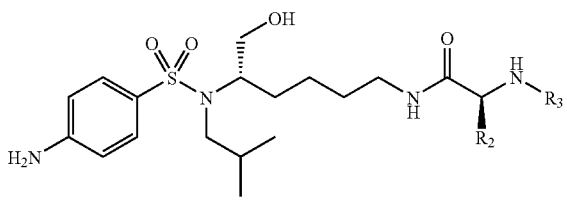

with a reagent mixture (e.g., metaphosphoric acid, polyphosphoric acid, polyphosphoric acid esters, phosphorous oxychloride, trimethylsilyl polyphosphate or equivalent thereof in the presence of an organic base in a solvent) for converting an alcohol functional group of the compound of formula I' into a phosphoester functional group and b) converting the phosphoester functional group of the resulting intermediate into a phosphonic acid functional group by reacting the resulting intermediate with an acid (e.g., hydrochloric acid or an equivalent thereof). In accordance with the present invention, X', Y', $R_2$, $R_3$, $R_4$, and $R_5$ are as defined herein and may be the same for both of the above formulas.

In accordance with the present invention step a) may be carried out at a temperature ranging from about 0° C. to about 40° C. (e.g., about 0° C. to about 30° C.). Further in accordance with the present invention, step a) may be carried out by dissolving compound I' in the polar aprotic solvent and triethyl phosphate followed by the addition of a dialkylchlorophosphate (e.g., diethyl chlorophosphate) and then metal hydride (e.g., sodium hydride). Step a) may also comprise extracting and purifying (isolating) the resulting intermediate (compound II).

Also in accordance with the present invention step b) may be carried out at a temperature ranging from about 0° C. to about 40° C. (e.g., about 0° C. to about 30° C.). Further in accordance with the present invention, step b) may be carried out by dissolving the intermediate of step a) in anhydrous dichloromethane or an equivalent thereof (i.e., solvent) and reacting with trimethylsilyl bromide (bromotrimethylsilane). Also in accordance with the present invention, step b) may also comprise a step of removing the solvent therefore providing compound III.

In a further aspect, the present invention provides a process for synthesizing a compound of formula IIa where $R_1$ is $(OH)_2P(O)$;

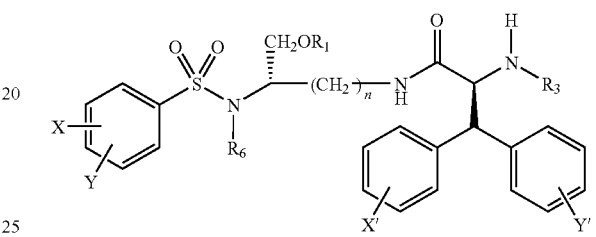

pharmaceutically acceptable salts and derivatives thereof (e.g., for example, when the compound of the present invention comprises an amino group, the pharmaceutically acceptable salt may be an ammonium salt), wherein X and Y, the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_4R_5$, —NHCOR_4, —$OR_4$, —$SR_4$, —$COOR_4$, —$COR_4$, and —$CH_2OH$ or X and Y together define an alkylenedioxy group selected from the group consisting of a methylenedioxy group of formula —$OCH_2O$— and an ethylenedioxy group of formula —$OCH_2CH_2O$—, wherein X' and Y', the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_4R_5$, —$NHCOR_4$, —$SR_4$, —$COR_4$ and —$CH_2OH$, and wherein n, $R_3$, $R_4$, $R_5$ and $R_6$ are as defined herein.

In accordance with the present invention, the process for synthesizing the above compounds of formula IIa may comprise the steps of a) reacting a compound of formula

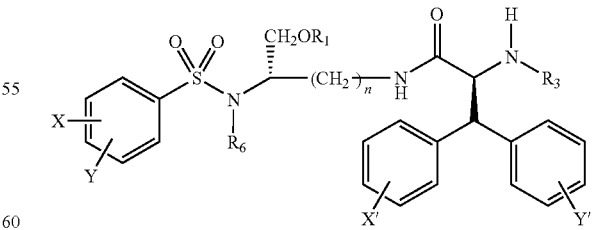

with a reagent mixture (e.g., metaphosphoric acid, polyphosphoric acid, polyphosphoric acid esters, phosphorous oxychloride, trimethylsilyl polyphosphate or equivalent thereof in the presence of an organic base in a solvent) for converting an alcohol functional group of the above compound into a phosphoester functional group and b) converting the phosphoester functional group of the resulting intermediate into a phosphonic acid functional group by reacting the resulting intermediate with an acid (e.g., hydrochloric acid).

In accordance with the present invention, X, Y, X', Y', n, $R_2$, $R_3$, $R_4$, $R_5$ and $R_6$ are as defined herein.

In accordance with the present invention step a) may be carried out at a temperature ranging from about 0° C. to about 40° C. (e.g., about 0° C. to about 30° C.). Further in accordance with the present invention, step a) may be carried out by dissolving the above described compound in a polar aprotic solvent (e.g., tetrahydrofurane, DMF, acetonitril, etc.) and triethyl phosphate followed by the addition of a dialkylchlorophosphate (e.g., diethyl chlorophosphate) and then metal hydride (e.g., sodium hydride). Step a) may also comprise extracting and purifying (isolating) the resulting intermediate.

Also in accordance with the present invention step b) may be carried out at a temperature ranging from about 0° C. to about 40° C. (e.g., about 0° C. to about 30° C.). Further in accordance with the present invention, step b) may be carried out by dissolving the intermediate of step a) in anhydrous dichloromethane (i.e., solvent) and reacting with trimethylsilyl bromide (bromotrimethylsilane). Also in accordance with the present invention, step b) may also comprise a step of removing the solvent therefore providing the above described compound The present invention provides in an additional aspect an improved process for synthesizing a compound of formula IIIA;

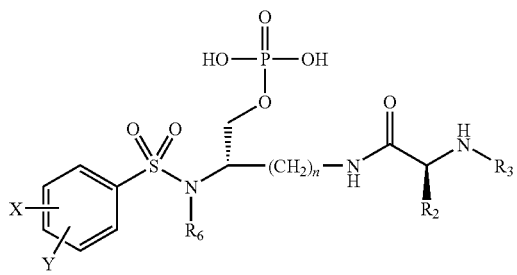

IIIA the process may comprise the step of acylating a compound of formula XIV

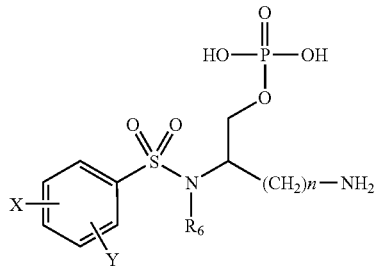

XIV with a reactive amino acid having structure:

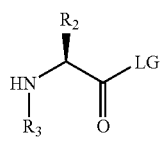

Where LG represents a leaving group which may be a halogen (e.g., F, Cl, Br, I), an azide, a symmetrical anhydride (e.g., —OCO—C($R_2$)($NR_3$)) wherein $R_2$ and $R_3$ are as described herein, a mixed anhydride, an active ester, a reactive hydroxylamine (e.g., N-hydroxysuccinimide) etc., such as those commonly known in the art (*Principles of peptide synthesis*, M. Bodansky, Springer-Verlag, 1984).

The absolute configuration of the amino acid may be R or S. The S form may yield some of the active compounds described herein.

The acylation step may be carried out at a temperature ranging from about 0° C. to about 40° C. (e.g., from about 0° C. to about 30° C.). More particularly, the acylating step may be carried out by a) increasing the alkalinity of an aqueous solution comprising a compound of formula XIV (e.g., with a base, e.g., sodium hydroxide) up to about pH 7-10 and b) adding a solution comprising the reactive amino acid in a polar aprotic solvent (e.g., acetone, THF, acetonitrile, DMF or any equivalent thereof) and allowing reaction between the compound of formula XIV and the reactive amino acid by agitation for a period of about 1-24 hours (or more) at a temperature of about 0° C. to about 40° C. Compound of formula IIIA may be isolated by extraction of the aqueous phase with a suitable solvent (e.g., ethyl acetate, chloroform, DCM, MEEK, isobutyl methyl ketone, TBDMK, halogenated solvents or any chemical equivalent thereof).

It is to be understood herein that a reaction time exceeding 24 hours or slightly less than 1 hour may be suitable to carry out the invention.

It is also to be understood herein that a temperature slightly exceeding 40° C. or slightly less than 0° C. may be suitable to carry out the invention.

In accordance with the present invention, the proportion of compound XIV and reactive amino acid may vary from about 2:1 to 1:2 or more particularly a proportion of about 1:1.1.

In accordance with the present invention, the aqueous phase may be acidified before being extracted with the suitable solvent (e.g., ethyl acetate). Acidification of the aqueous phase may be performed, for example by adjusting the pH to <2 with a strong acid (e.g., HCl, phosphoric acid, sulfuric acid, TFA solutions, etc.).

In accordance with the present invention, the suitable solvent may be evaporated, thereby providing a substantially pure powder of the compound of formula IIIA.

Also in accordance with the present invention, X, Y, X', Y', n, $R_2$, $R_3$, $R_4$, $R_5$ and $R_6$ are as defined herein and may be the same for the above mentioned formulas.

Additionally, when X, Y, X', Y', $R_2$, $R_3$, $R_4$, $R_5$ and $R_6$ comprise a reactive group (e.g., —$NH_2$ etc.), it is to be understood herein that a protective group, such as for example, a carbamate (e.g. Boc), an amide (e.g. Ac), a phosphonate (e.g. —P(O)(OEt)$_2$, may transiently be attached during the synthesis process.

Therefore, when X and/or Y are for example $NR_4R_5$, $R_4$ and/or $R_5$ may also be a protective group selected from the group consisting of for example, a carbamate (e.g. Boc (tert-butoxycarbonyl)), an amide (e.g. Acetyl), a phosphonate (e.g. —P(O)(OEt)$_2$, which may transiently be present during the synthesis process and which may be converted into a $NH_2$ group upon hydrolysis.

In accordance with another embodiment of the invention, X and Y, the same or different, may be, more specifically selected from the group consisting of methyl, ethyl, H, F, Cl, Br, I and —$NR_4R_5$.

In accordance with the present invention $R_4$ and $R_5$, the same or different, may be for example, H or a protective group.

More particularly, X and Y, the same or different, may be for example, H, F or $NH_2$.

In accordance with a further embodiment of the invention, $R_6$ may be, more particularly, selected from the group consisting of a straight alkyl group of 1 to 6 carbon atoms and a branched alkyl group of 3 to 6 carbon atoms. More particularly, $R_6$ may be for example, iso-butyl.

In accordance with yet a further embodiment of the invention, $R_3$ may be, more specifically a group of formula $R_{3A}$—CO—, where $R_{3A}$ may be selected, for example, from the group consisting of a straight or branched alkyl group of 1 to 6 carbon atoms (e.g. methyl, ethyl-, propyl, iso-propyl, butyl, iso-butyl, tert-butyl, tert-butyl-$CH_2$—, etc.), an alkyloxy group of 1 to 6 carbon atoms. In accordance with the present invention $R_{3A}$ may be, for example, a straight alkyl group of 1 to 6 carbon atoms or even more particularly methyl, ethyl or propyl.

In accordance with an additional embodiment of the invention, $R_2$ may be more particularly a diphenylmethyl group (substituted with X' and/or Y' or unsubstituted).

In accordance with yet an additional embodiment of the invention, $R_2$ may more particularly be a naphthyl-1-$CH_2$— group or a naphthyl-2-$CH_2$— (substituted with X' and/or Y' or unsubstituted).

Also in accordance with a further embodiment, X' and Y', the same or different, may be selected, for example, from the group consisting of H, methyl, ethyl, F, Cl, Br, I and —$NR_4R_5$. More particularly, X' and Y' may be H.

The present invention relates in a further aspect thereof to an improved process for synthesizing a compound of formula III

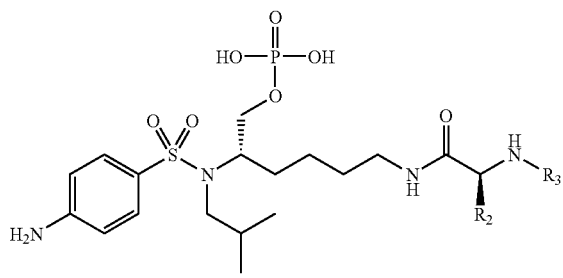

the process may comprise the steps of acylating a compound of formula XIX

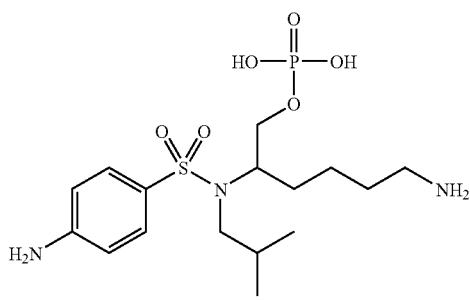

with a reactive amino acid having structure:

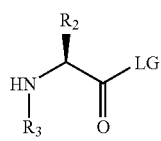

where LG represents a leaving group which may be a halogen, e.g., F, Cl, Br, I, an azide, a symmetrical anhydride (e.g., —OCO—C($R_2$)($NR_3$)) wherein $R_2$ and $R_3$ are as described herein, a mixed anhydride, an active ester, a reactive hydroxylamine (e.g., N-hydroxysuccinimide) to such as those commonly known in the art (Principles of peptide synthesis, M. Bodansky, Springer-Verlag, 1984 the entire content of which is incorporated herein by reference).

The absolute configuration of the amino acid may be R or S. The S form may yield some of the active compounds described herein.

The acylation step may be carried out at a temperature ranging from about 0° C. to about 40° C. (e.g., from about 0° C. to about 30° C.). More particularly, the acylating step may be carried out by a) increasing the alkalinity of an aqueous solution comprising a compound of formula XIX (with a base, e.g., sodium hydroxide) up to pH 7 to pH 10 and b) adding a solution comprising the reactive amino acid in a dipolar aprotic solvent (e.g., acetone, THF, acetonitrile, etc.) and allowing reaction between the compound of formula XIX and the reactive amino acid by agitation of the mixture for a period of 1 to 24 hours at a temperature of from about 0° C. to about 40° C. Compound of formula III may be isolated by extraction of the aqueous phase with a suitable solvent (e.g., ethyl acetate, chloroform, DCM, MEEK, isobutyl methyl ketone, TBDMK, halogenated solvents or any chemical equivalent thereof).

In accordance with the present invention, the proportion of compound XIX and reactive amino acid may vary from about 2:1 to 1:2 or more particularly about 1:1.1.

In accordance with the present invention, the aqueous phase may be acidified before being extracted with the suitable solvent (e.g., ethyl acetate). Acidification of the aqueous phase may be performed, for example by adjusting the pH to <2 with a strong acid (e.g., HCl, phosphoric acid, sulfuric acid, TFA solutions, etc.).

In accordance with the present invention, the suitable solvent may be evaporated, thereby providing a substantially pure powder of the compound of formula III.

An exemplary reactive amino acid may include, for example, a compound of formula

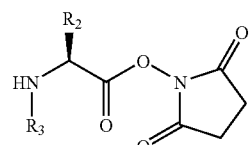

In accordance with the present invention, X', Y', $R_2$, $R_3$, $R_4$, and $R_5$ are as defined herein and may be the same for the above mentioned formulas.

In accordance with an embodiment of the invention, $R_3$ may be, more specifically a group of formula $R_{3A}$—CO—, where $R_{3A}$ may be selected, for example, from the group consisting of a straight or branched alkyl group of 1 to 6 carbon atoms (e.g. methyl, ethyl-, propyl, iso-propyl, butyl, iso-butyl, tert-butyl, tert-butyl-$CH_2$—, etc.), an alkyloxy group of 1 to 6 carbon atoms. In accordance with the present invention $R_{3A}$ may be, for example, a straight alkyl group of 1 to 6 carbon atoms or even more particularly methyl, ethyl or propyl.

In accordance with an additional embodiment of the invention, $R_2$ may be more particularly a diphenylmethyl group (substituted with X' and/or Y' or unsubstituted).

In accordance with yet an additional embodiment of the invention, $R_2$ may more particularly be a naphthyl-1-$CH_2$— group or a naphthyl-2-$CH_2$— (substituted with X' and/or Y' or unsubstituted).

Also in accordance with a further embodiment, X' and Y', the same or different, may be selected, for example, from the group consisting of H, methyl, ethyl, F, Cl, Br, I and —$NR_4R_5$. More particularly, X' and Y' may be H.

In an additional aspect, the present invention relates to an improved process for synthesizing a compound of formula IIa as described herein, wherein $R_1$ is $(HO)_2P(O)$ and wherein $R_3$ is $CH_3OCO$, the process may comprise the step of acylating a compound of formula XIV

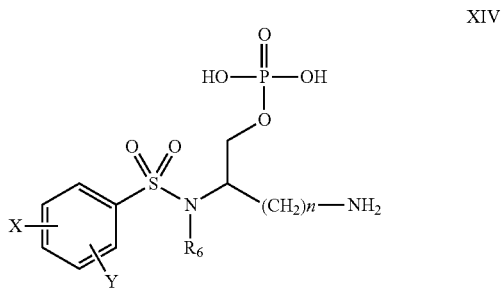

XIV with a reactive amino acid having the following structure

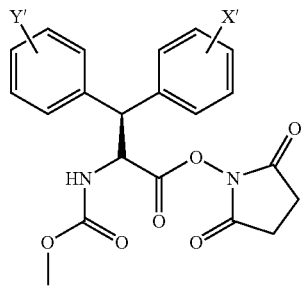

In accordance with the present invention, X, Y, X', Y', n, $R_4$, $R_5$ and $R_6$ are as defined herein and may be the same for the above mentioned formulas.

When X, Y, X', Y', $R_4$, $R_5$ and $R_6$ comprise a reactive group (e.g., —$NH_2$ etc.), it is to be understood herein that a protective group such as for example a carbamate (e.g. Boc), an amide (e.g. Ac), a phosphonate (e.g. —$P(O)(OEt)_2$), may transiently be attached during the synthesis process.

Therefore, when X and/or Y are for example $NR_4R_5$, $R_4$ and/or $R_5$ may also be a protective group selected from the group consisting of for example, a carbamate (e.g. Boc (tert-butoxycarbonyl)), an amide (e.g. Acetyl), a phosphonate (e.g. —$P(O)(OEt)_2$, which may transiently be present during the synthesis process and which may converted into a $NH_2$ group upon hydrolysis.

The acylation step may be carried out at a temperature ranging from about 0° C. to about 40° C. (e.g., from about 0° C. to about 30° C.). More particularly, the acylating step may be carried out by a) increasing the alkalinity of an aqueous solution comprising a compound of formula XIV (with a base, e.g., sodium hydroxide) up to about pH 7 to about pH 10 and b) adding a solution comprising the reactive amino acid in a dipolar aprotic solvent (e.g., acetone, THF, acetonitrile, or an equivalent thereof) and allowing reaction between the compound of formula XIV and the reactive amino acid by agitation for a period of 1 to 24 hours or more at a temperature of from about 0° C. to about 40° C. Compound of formula IIa may be isolated by extraction of the aqueous phase with a suitable solvent (e.g., ethyl acetate, chloroform, DCM, MEEK, isobutyl methyl ketone, TBDMK, halogenated solvents or any chemical equivalent thereof).

In accordance with the present invention, the proportion of compound XIX and reactive amino acid may vary from about 2:1 to 1:2 or more particularly a proportion of about 1:1.1.

In accordance with the present invention, the aqueous phase may be acidified before being extracted with the suitable solvent (e.g., ethyl acetate). Acidification of the aqueous phase may be performed, for example by adjusting the pH to <2 with a strong acid (e.g., HCl, phosphoric acid, sulfuric acid, TFA solutions, etc.).

In accordance with the present invention, the suitable solvent may be evaporated, thereby providing a substantially pure powder of the compound of formula IIa.

In accordance with another embodiment of the invention, X and Y, the same or different, may be, more specifically selected from the group consisting of methyl, ethyl, H, F, Cl, Br, I and —$NR_4R_5$.

In accordance with the present invention $R_4$ and $R_5$, the same or different, may be for example, H, tert-butoxycarbonyl, etc.

More particularly, X and Y, the same or different, may be for example, H, F or $NH_2$.

In accordance with a further embodiment of the invention, $R_6$ may be, more particularly, selected from the group consisting of a straight alkyl group of 1 to 6 carbon atoms and a branched alkyl group of 3 to 6 carbon atoms. More particularly, $R_6$ may be for example, iso-butyl.

Also in accordance with yet a further embodiment, X' and Y', the same or different, may be selected, for example, from the group consisting of H, methyl, ethyl, F, Cl, Br, I and —$NR_4R_5$. More particularly, X' and Y' may be H.

In accordance with an embodiment of the present invention, a PL-461 compound of formula IIIB;

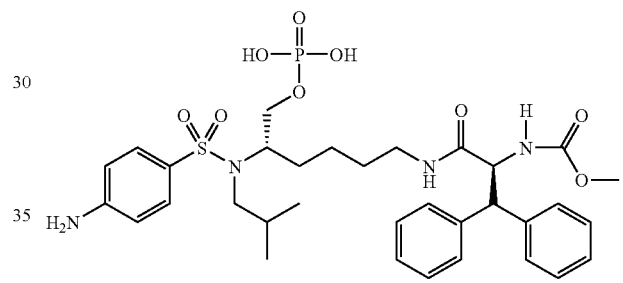

IIIB may be synthesized using a process which may comprise the step of acylating a compound of formula XIX

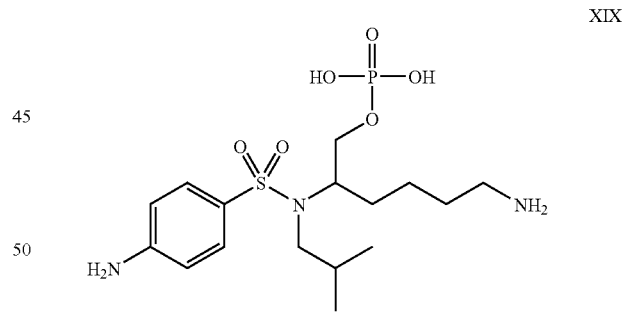

XIX with a reactive amino acid of formula

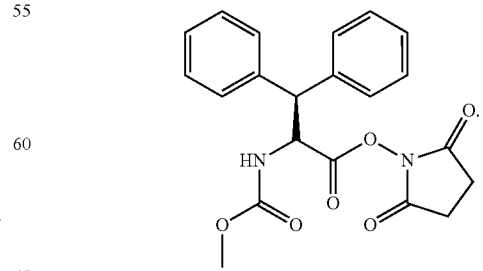

The acylation step may be carried out at a temperature ranging from about 0° C. to about 40° C. (e.g., from about 0°

C. to about 30° C.). More particularly, the acylating step may be carried out by a) increasing the alkalinity of an aqueous solution comprising a compound of formula XIX (e.g., with a base, e.g., sodium hydroxide) up to about pH 7 to about pH 10 and b) adding a solution comprising the reactive amino acid in a dipolar aprotic solvent (e.g., acetone, THF, acetonitrile, or any equivalent thereof) and allowing reaction between the compound of formula XIX and the reactive amino acid by agitation for a period of about 1 to about 24 hours or more at a temperature of about 0° C. to about 40° C. The PL-461 compound may be isolated by extraction of the aqueous phase with a suitable solvent (e.g., ethyl acetate, chloroform, DCM, MEEK, isobutyl methyl ketone, TBDMK, halogenated solvents or any chemical equivalent thereof).

In accordance with the present invention, the proportion of compound XIX and reactive amino acid may vary from about 2:1 to 1:2 or more particularly in a proportion of about 1:1.1.

In accordance with the present invention, the aqueous phase may be acidified before being extracted with the suitable solvent (e.g., ethyl acetate). Acidification of the aqueous phase may be performed, for example by adjusting the pH to <2 with a strong acid (e.g., HCl, phosphoric acid, sulfuric acid, TFA solutions, etc.).

In accordance with the present invention, the suitable solvent may be evaporated, thereby providing a substantially pure powder of the PL-461 compound.

Further in accordance with the present invention, a PL-462 compound of formula

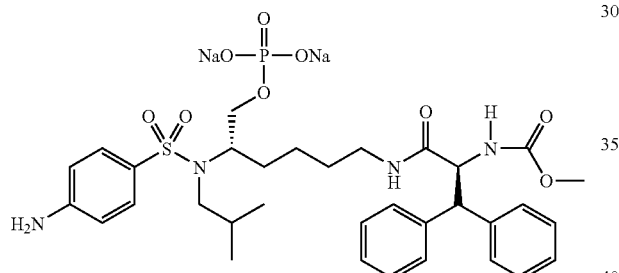

may be synthesized using a process which may comprise the step of reacting a free acid of PL-461 with a sodium base. Other alkali metal salts may be prepared by treating the PL-461 compound with a corresponding alkali metal base. Also in accordance with the invention, divalent metals such as Ca, Mg, Zn, etc. (e.g., as acetate salts) may be used to make the corresponding PL462-salts.

More particularly, the present invention relates to a process for the preparation of compound of formula IIIB (PL-461)

IIIB

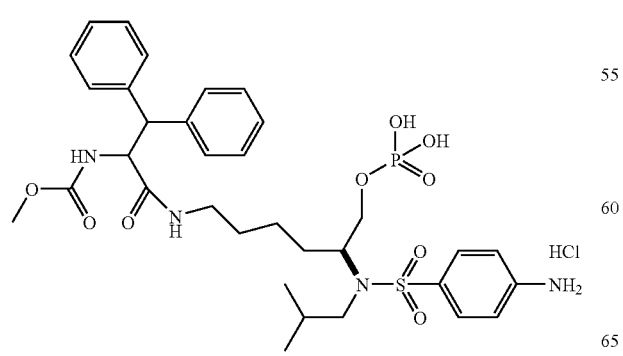

the process may comprise the steps of
a) phosphorylating a compound of formula XVII

XVII

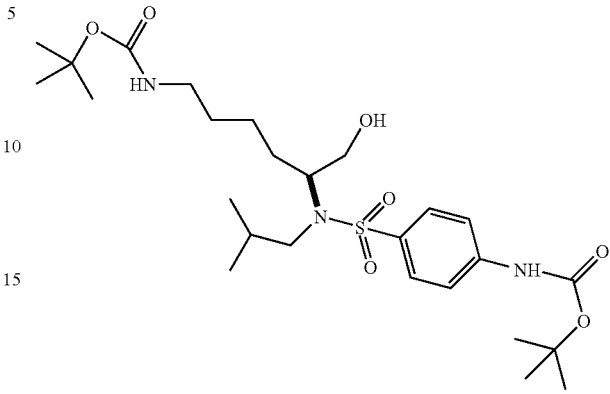

with for example, metaphosphoric acid, polyphosphoric acid, polyphosphoric acid esters, trimethylsilyl polyphosphate, phosphorous oxychloride or equivalent thereof, in the presence of an organic base (e.g., a tertiary amine (e.g. pyridine, etc.)), in a dipolar aprotic solvent (e.g., MiBK, acetone, etc.);
b) hydrolyzing the compound of a) in the presence of concentrated hydrochloric acid to give a water soluble hydrochloric salt of phosphoric acid mono ester, and;
c) acylating the compound of step b) comprised in an aqueous solution with a suitable reactive amino acid as described herein to provide the phosphate mono ester of formula IIIB

IIIB

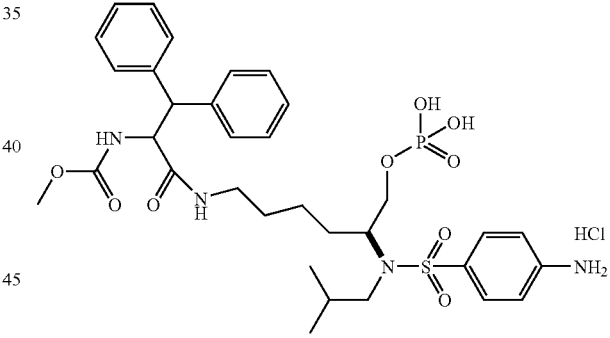

In accordance with the present invention, the dipolar aprotic solvent may be, for example, methyl iso-butyl ketone or acetone.

In accordance with the present invention, the suitable reactive amino acid may be, for example, a compound of formula:

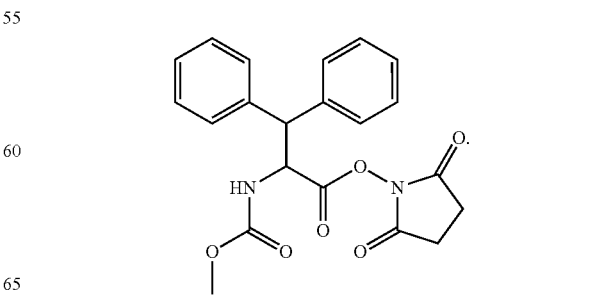

In accordance with another embodiment of the present invention, a PL-515 compound of formula;

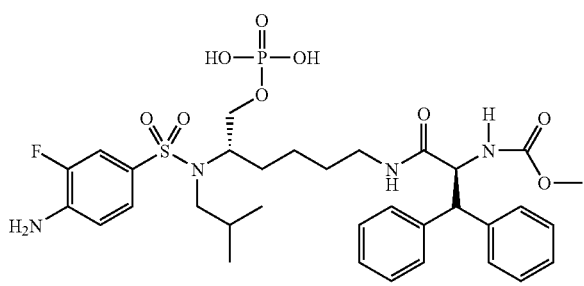

may be synthesized using a process which may comprise the step of acylating a compound of formula XIX'

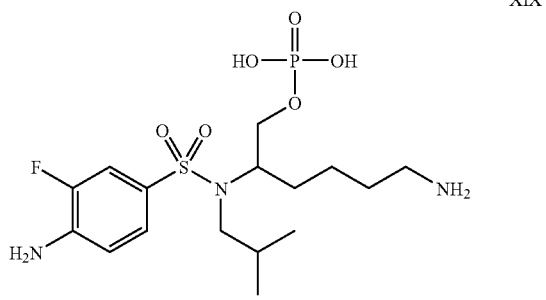

XIX' with a reactive amino acid of formula

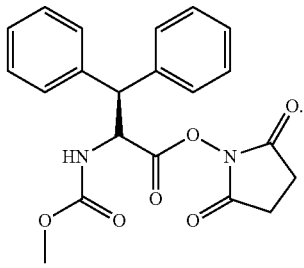

The acylation step may be carried out at a temperature ranging from about 0° C. to about 40° C. (e.g., from about 0° C. to about 30° C.). More particularly, the acylating step may be carried out by a) increasing the alkalinity of an aqueous solution comprising a compound of formula XIX' (e.g., with a base, e.g., sodium hydroxide) up to about pH 7 to about pH 10 and b) adding a solution comprising the reactive amino acid in a dipolar aprotic solvent (e.g., acetone, THF, acetonitrile or any equivalent thereof) and allowing reaction between the compound of formula XIX' and the reactive amino acid by agitation for a period of about 1 to about 24 hours at a temperature of about 0° C. to about 40° C. The compound PL-515 may be isolated by extraction of the aqueous phase with a suitable solvent (e.g., ethyl acetate, chloroform, DCM, MEEK, TBDMK, isobutyl methyl ketone, halogenated solvents or any equivalent thereof).

In accordance with the present invention, the proportion of compound XIX' and reactive amino acid may vary from about 2:1 to 1:2 or more particularly in a proportion of about 1:1.1.

In accordance with the present invention, the aqueous phase may be acidified before being extracted with the suitable solvent. Acidification of the aqueous phase may be performed, for example by adjusting the pH to <2 with a strong acid (e.g., HCl, phosphoric acid, sulfuric acid, TFA solutions, etc.).

In accordance with the present invention, the suitable solvent may be evaporated, thereby providing a substantially pure powder of the compound PL-515.

An alkali metal salt of PL-515 may be prepared as indicated for PL-462.

Alternatively, PL-515 may be generated by selective fluorination (e.g., using an electrophilic fluorinating compound) of the PL-461 compound.

The present invention in further aspects, provides novel intermediates, their synthesis and their use in the preparation of the lysine based compounds, derivatives and pharmaceutically acceptable salts described herein.

In another aspect, the present invention relates to intermediates of formula XV' useful to generate several compounds described herein including their derivatives and pharmaceutically acceptable salts thereof;

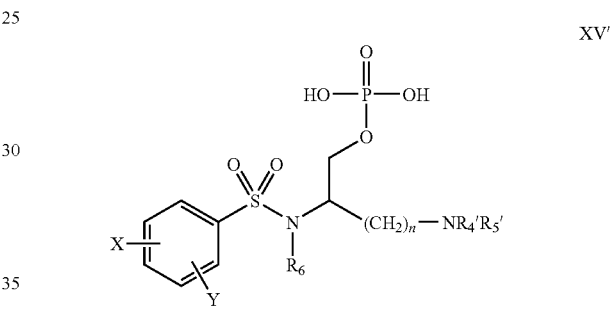

XV' wherein n may be 3 or 4;
wherein X and Y, the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_4R_5$, —NH-$COR_4$, —$SR_4$, —$COOR_4$, —$COR_4$, and —$CH_2OH$ or X and Y together define an alkylenedioxy group selected from the group consisting of a methylenedioxy group of formula —$OCH_2O$— and an ethylenedioxy group of formula —$OCH_2CH_2O$—,
wherein $R_6$ may be selected, for example, from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof,
wherein $R_4$ and $R_5$, the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms and a protective group selected from the group consisting of a carbamate (e.g. Boc), an amide (e.g. Ac), a phosphonate (e.g. —$P(O)(OEt)_2$,
wherein $R_4'$ and $R_5'$, the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, and a protective group selected from the group consisting of a carbamate (e.g. Boc), an amide (e.g. Ac), a phosphonate (e.g. —$P(O)(OEt)_2$, The present invention therefore provides a compound of formula XV' wherein n may be, more particularly, 4.

The present invention also provides a compound of formula XV' where X and Y, the same or different, may be, more specifically selected from the group consisting of methyl, ethyl, H, F, Cl, Br, I and —$NR_4R_5$.

In accordance with the present invention at least one of $R_4$ or $R_5$ is a protective group.

In accordance with the present invention X and Y, the same or different, may be for example, H, F or $NH_2$.

In accordance with the present invention $R_4$ and $R_5$, the same or different, may be for example, H or a protective group.

The present invention also provides a compound of formula XV' where $R_4'$ and $R_5'$, the same or different, may be selected, for example, from the group consisting of H and a protective group.

The present invention further provides a compound of formula XV' where $R_6$ may be, more particularly, selected from the group consisting of a straight alkyl group of 1 to 6 carbon atoms and a branched alkyl group of 3 to 6 carbon atoms. In accordance with the present invention $R_6$ may be for example, iso-butyl.

For example, compounds of the present invention, include, without limitation, the following;
a compound of formula XV' wherein n is 4, X is $NH_2$, Y is H or F, X' is H, Y' is H, $R_4$ is H and $R_5$—, is H and $R_6$ is iso-butyl;
a compound of formula XV' wherein n is 4, X is 4-$NH_2$, Y is H, X' is H, Y' is H, $R_{4'}$ is H and $R_{5'}$, and $R_6$ is iso-butyl;
a compound of formula XV', wherein n is 4, X is 4-$NH_2$, Y is 3-F, X' is H, Y' is H, $R_{4'}$ is H and $R_{5'}$, and $R_6$ is iso-butyl;
a compound of formula XV' wherein n is 4, X is $NH_2$, Y is H or F, X' is H, Y' is H, $R_{4'}$ is H and $R_{5'}$ is a protective group and $R_6$ is iso-butyl;
a compound of formula XV' wherein n is 4, X is $NH_2$, Y is H or F, X' is H, Y' is H, $R_{4'}$ is H, $R_{5'}$ is H and $R_6$ is iso-butyl;
a compound of formula XV' wherein n is 4, X is 4-$NH_2$, Y is H, X' is H, Y' is H, $R_{4'}$ is H, $R_{5'}$ is a protective group and $R_6$ is iso-butyl;

In an additional aspect, the present invention relates to intermediates of formula XIV useful to generate several compounds described herein including their derivatives and pharmaceutically acceptable salts thereof;

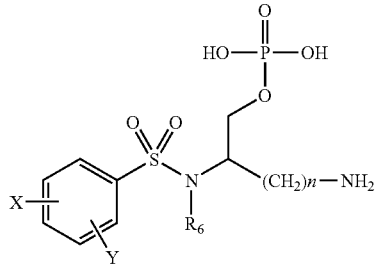

XIV wherein n may be 3 or 4,
wherein X and Y, the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_4R_5$, —NH-$COR_4$, —$OR_4$, —$SR_a$, —$COOR_4$, —$COR_4$, and —$CH_2OH$ or X and Y together define an alkylenedioxy group selected from the group consisting of a methylenedioxy group of formula —$OCH_2O$— and an ethylenedioxy group of formula —$OCH_2CH_2O$—, wherein $R_6$ may be selected, for example, from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof, and;

wherein $R_4$ and $R_5$, the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, and a protective group selected from the group consisting of a carbamate (e.g. Boc), an amide (e.g. Ac), a phosphonate (e.g. —P(O)(OEt)$_2$, The present invention therefore provides a compound of formula XIV wherein n may be, more particularly, 4.

The present invention also provides a compound of formula XIV where X and Y, the same or different, may be, more specifically selected from the group consisting of methyl, ethyl, H, F, Cl, Br, I and —$NR_4R_5$.

In accordance with the present invention, at least one of $R_4$ or $R_5$ is a protective group.

In accordance with the present invention X and Y, the same or different, may be for example, H, F or $NH_2$.

In accordance with the present invention $R_4$ and $R_5$, the same or different, may be for example, H or a protective group.

The present invention also provides a compound of formula XIV where $R_6$ may be, more particularly, selected from the group consisting of a straight alkyl group of 1 to 6 carbon atoms and a branched alkyl group of 3 to 6 carbon atoms. In accordance with the present invention $R_6$ may be for example, iso-butyl.

In an additional aspect, the present invention relates to intermediates of formula XV useful to generate several compounds described herein including their derivatives and pharmaceutically acceptable salts thereof;

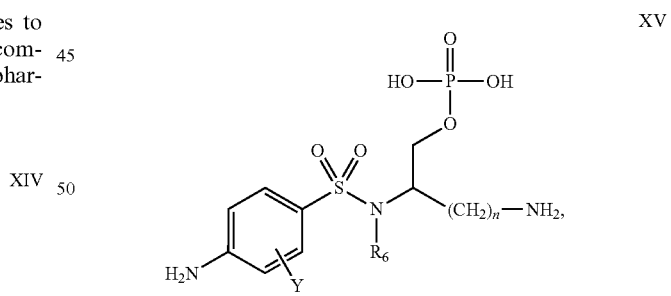

XV wherein n may be 3 or 4
wherein Y may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_4R_5$, —$NHCOR_4$, —$OR_4$, —$SR_4$, —$COOR_4$, —$COR_4$, and —$CH_2OH$;
wherein $R_6$ may be selected, for example, from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof, and;

wherein $R_4$ and $R_5$, the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, and tert-butoxycarbonyl.

The present invention therefore provides a compound of formula XV wherein n may be, more particularly, 4.

The present invention also provides a compound of formula XV where Y may be, more specifically selected from the group consisting of methyl, ethyl, H, F, Cl, Br, I and —$NR_4R_5$.

In accordance with the present invention Y may be for example, H, F, Cl, or Br. More particularly, Y may be at position 3. For example Y may be 3-F.

The present invention also provides a compound of formula XV where $R_6$ may be, more particularly, selected from the group consisting of a straight alkyl group of 1 to 6 carbon atoms and a branched alkyl group of 3 to 6 carbon atoms. In accordance with the present invention $R_6$ may be for example, iso-butyl.

In a further aspect, the present invention relates to intermediates of formula XVI useful to generate several compounds described herein including their derivatives and pharmaceutically acceptable salts thereof;

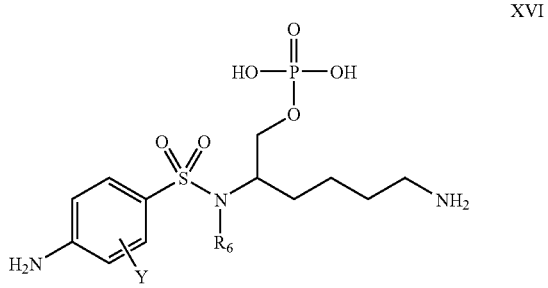

XVI wherein Y may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_4R_5$, —$NHCOR_4$, —$OR_4$, —$SR_4$, —$COOR_4$, —$COR_4$, and —$CH_2OH$
wherein $R_6$ may be selected, for example, from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof, and; wherein $R_4$ and $R_5$, the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms and tert-butoxycarbonyl.

The present invention also provides a compound of formula XVI where Y may be, more specifically selected from the group consisting of methyl, ethyl, H, F, Cl, Br, I and —$NR_4R_5$.

In accordance with the present invention Y may be for example, H, F, Cl, or Br.

The present invention also provides a compound of formula XVI where $R_6$ may be, more particularly, selected from the group consisting of a straight alkyl group of 1 to 6 carbon atoms and a branched alkyl group of 3 to 6 carbon atoms. In accordance with the present invention $R_6$ may be for example, iso-butyl.

In accordance with an embodiment of the present invention more particularly relates to an intermediate of formula XIX

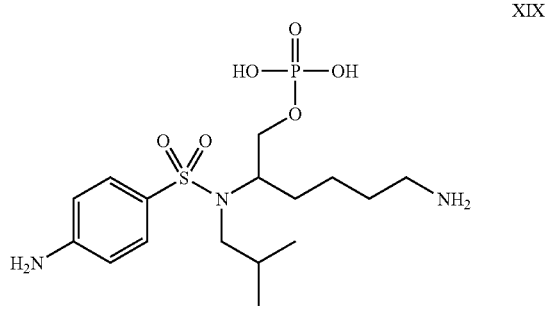

XIX

In yet an additional aspect, the present invention relates to the use of at least one intermediate of formula XIV, XV, XV, XVI, XIX and/or XIX' in the manufacture of a drug (or pharmaceutical composition) comprising at least one compound described herein as well as derivatives and pharmaceutically acceptable salts thereof.

The terms "HIV protease" and "HIV aspartyl protease" are used interchangeably and include the aspartyl protease encoded by the human immunodeficiency virus type 1 or 2.

The terms "pharmaceutically acceptable carrier", "pharmaceutically acceptable adjuvant" and "physiologically acceptable vehicle" refer to a non-toxic carrier or adjuvant that may be administered to a patient, together with one or more compounds of the present invention, and which does not destroy the pharmacological activity thereof.

A "pharmaceutically acceptable derivative" means any pharmaceutically acceptable salt (e.g. ammonium salt, etc.), ester, or salt of such ester, of a compound of this invention or any other compound which, upon administration to a recipient, is capable of providing (directly or indirectly) a compound of this invention or an antivirally active metabolite or residue thereof.

It is to be understood herein that a "straight alkyl group of 1 to 6 carbon atoms" includes for example, methyl, ethyl, propyl, butyl, pentyl and hexyl.

It is to be understood herein that a "branched alkyl group of 3 to 6 carbon atoms" includes for example, without limitation, iso-butyl, tert-butyl, 2-pentyl, 3-pentyl, etc.

It is to be understood herein, that a "cycloalkyl group having 3 to 6 carbon" includes for example, without limitation, cyclopropyl, cyclobutyl, cyclopentyl, cyclocyclohexyl (i.e., $C_6H_{11}$).

The term "pharmaceutically acceptable salt" refers to either a basic addition salt or an acid addition salt.

The expression "pharmaceutically acceptable acid addition salts" is intended to apply to any non-toxic organic or inorganic acid addition salt of a base compound or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as methanesulfonic acid and 2-hydroxyethane sulfonic acid. Such salts can exist in either a hydrated or substantially anhydrous form.

The expression "pharmaceutically acceptable basic addition salts" is intended to apply to any non-toxic organic or inorganic basic addition salts of a compound or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts may be formed with those compounds.

Salts derived from appropriate bases include alkali metal (e.g., sodium), alkaline earth metal (e.g., magnesium), ammonium and N—$(C_{1-4}$ alkyl$)_4^+$ salts.

The compounds of this invention contain one or more asymmetric carbon atoms and thus may occur as racemates and racemic mixtures, single enantiomer, diastereomeric mixtures and individual diastereoisomers. All such isomeric forms of these compounds are expressly included in the present invention. Each stereogenic carbon may be of the R or S configuration.

Pharmaceutically acceptable salts of the compounds of this invention include those derived from pharmaceutically acceptable inorganic and organic acids and bases. Examples of such acid salts include: acetate, adipate, alginate, aspartate, benzoate, benzenesulfonate, bisulfate, butyrate, citrate, camphorate, camphorsulfonate, cyclopentanepropionate, digluconate, do decylhydrogensulfate, dodecylsulfate, ethanesulfonate, formate, fumarate, glucoheptanoate, glycerophosphate, glycollate, hemisulfate, heptanoate, hexanoate, hydrochloride, hydrobromide, hydroiodide, 2-hydroxyethanesulfonate, lactate, maleate, malonate, methanesulfonate, 2-naphthylsulfonate, nicotinate, nitrate, oxalate, pamoate, pectinate, perchlorate, persulfate, 3-phenylpropionate, phosphate, picrate, pivalate, propionate, salicylate, succinate, sulfate, tartrate, thiocyanate, tosylate, and undecanoate.

This invention also envisions the quaternization of any basic nitrogen containing groups of the compounds disclosed herein. The basic nitrogen may be quaternized with any agents known to those of ordinary skill in the art including, for example, lower alkyl halides, such as methyl, ethyl, propyl and butyl chlorides, bromides and iodides; dialkyl sulfates including dimethyl, diethyl, dibutyl and diamyl sulfates; long chain halides such as decyl, lauryl, myristyl and stearyl chlorides, bromides and iodides, and aralkyl halides including benzyl and phenethyl bromides. Water or oil-soluble or dispersible products may be obtained by such quaternization.

It is to be understood herein, that if a "range" or "group of substances" is mentioned with respect to a particular characteristic (e.g., temperature, concentration, time and the like) of the present invention, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein. Thus, for example, with respect to the number of carbon atoms, the mention of the range of 1 to 6 carbon atoms is to be understood herein as incorporating each and every individual number of carbon atoms as well as sub-ranges such as, for example, 1 carbon atoms, 3 carbon atoms, 4 to 6 carbon atoms, etc.

with respect to reaction time, a time of between 1 to 24 hours or more, is to be understood as specifically incorporating herein each and every individual time, as well as sub-range, between and including 1 and 24 hours, such as for example 1.5 hours, 12 hours, 22.25 hours, etc., with respect to a temperature range of from about 0° C. to about 40° C., it is to be understood herein as specifically incorporating herein each and every individual temperature, as well as sub-range, between and including 0° C. and 40° C., such as for example 4° C., 4.5° C., 16° C., 20° C., 22° C., 32.7° C., etc.

a temperature range of about 0° C. to about 40° C. also includes, for example, ranges of between about 0° C. and about 35° C., between about 0° C. and about 30° C., between about 0° C. and about 22° C., between about 10° C. and about 25° C. etc.

and similarly with respect to other parameters such as concentrations, elements, etc. . . . .

It is in particular to be understood herein that the compound formulae each include each and every individual compound described thereby as well as each and every possible class or sub-group or sub-class of compounds whether such class or sub-class is defined as positively including particular compounds, as excluding particular compounds or a combination thereof; for example an exclusionary definition for the formula (e.g. I) may read as follows: "provided that when one of A or B is —COOH and the other is H, —COOH may not occupy the 4' position".

It is also to be understood herein that "g" or "gm" is a reference to the gram weight unit and "C", or "° C." is a reference to the Celsius temperature unit.

BRIEF DESCRIPTION OF THE DRAWINGS

In drawings which illustrates exemplary embodiments of the present invention.

DETAILED DESCRIPTION OF THE INVENTION

Figure 1:
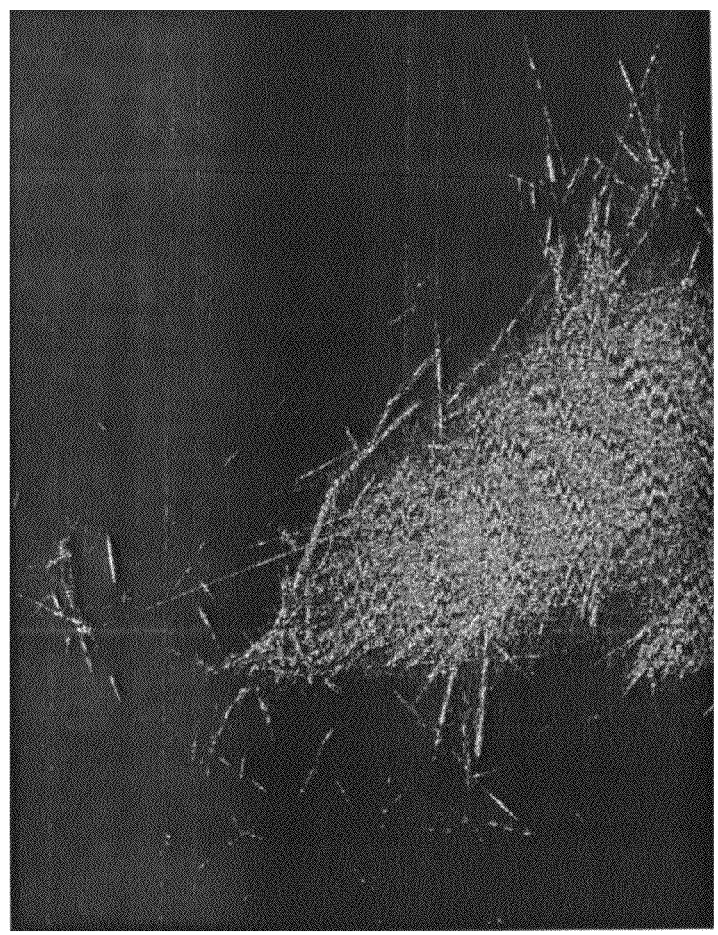
FIG. 1 is a microscopic image of the PL-462 compound in aqueous solution (magnification of 200×)

The compounds of the present invention may be prepared using conventional techniques from readily available starting materials. The detailed descriptions of these approaches are presented below. However, improved processes are described more particularly in schemes 2B, 2C and 2D below.

Scheme 1 illustrates a generic example for the preparation of the phosphate monoester III derived from a primary alcohol (see I), a compound of HIV protease inhibitors (see example 1 (step G and H) in the experimental portion of this document for a specific example of this synthesis).

Note:

a) $R_2$ and $R_3$ are as defined herein.

The synthesis of phosphate monoester III may use a HIV aspartyl protease inhibitor (I', see U.S. Pat. No. 6,632,816 (identified as 1)) as the starting material. The diethyl phosphotriester II was obtained in good yield upon treatment with diethyl chlorophosphate and sodium hydride in a mixture of tetrahydrofuran and triethylphosphate. Then, addition of trimethylsilyl bromide in dichloromethane (DCM) gave compound III in good to excellent yields.

Scheme 1
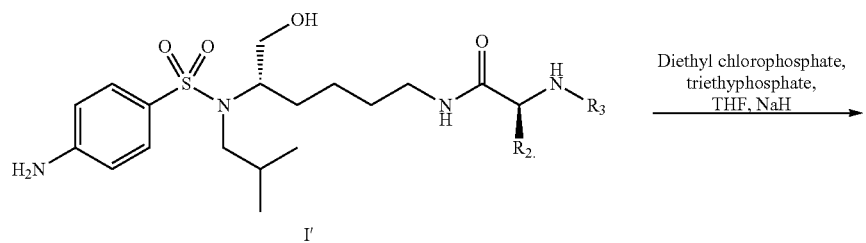
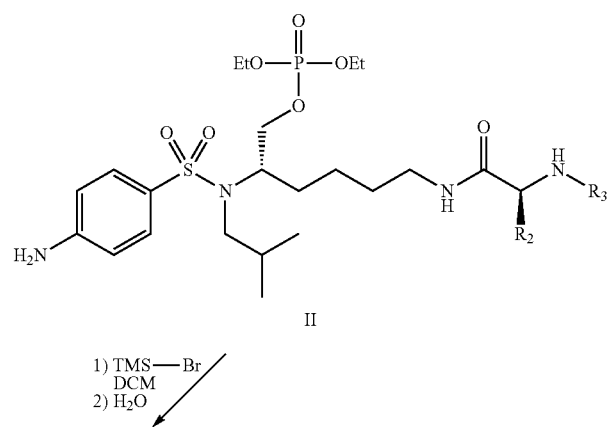
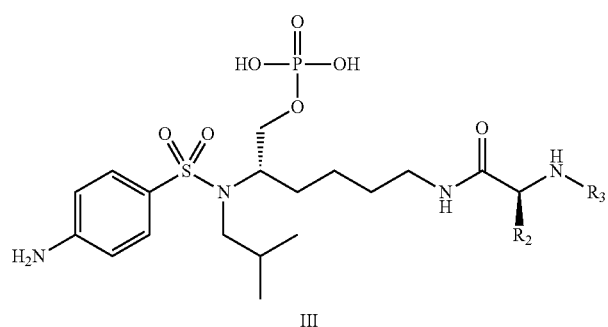
Scheme 1A represents another generic example for the preparation of the phosphate monoester IIIA derived from a primary alcohol (see IA), a compound of HIV protease inhibitors.

Note:
a) n, X, Y, $R_2$, $R_3$ and $R_6$ are as defined herein.

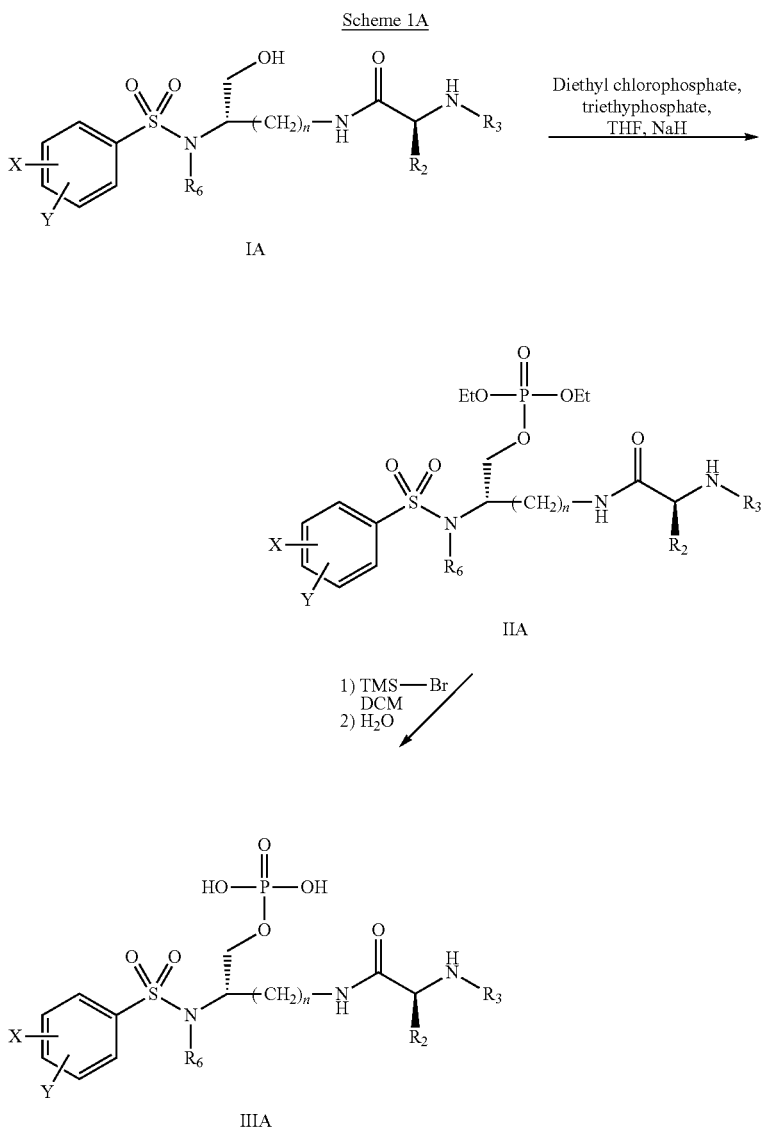

Scheme 1A

The synthesis of phosphate monoester IIIA is performed as described for the preparation of III (scheme 1).

Scheme 2A illustrates a generic example for the preparation of the phosphate monoester a compound of HIV protease inhibitors, with a different approach starting from (3S)-3-isobutylamino-azepan-2-one (IV).

Note:
a) $R_2$ and $R_3$ are as defined herein.

As shown in scheme 2A, the phosphate monoester derivative III was obtained from (3S)-3-isobutylamino-azepan-2-one (IV) in a seven-step reaction sequence. Initially, (2S)-3-isobutylamino-azepan-2-one (IV) was sulfonated with 4-acetamidobenzenesulfonyl chloride in the presence of triethylamine in dichloromethane to give compound V in excellent yields. The derivative VI was obtained quantitatively upon treatment of V with di-tert-butyl pyrocarbonate and DMAP in acetonitrile. The reductive ring opening with sodium borohydride in ethanol lead to key intermediates VII in good yield. The diethyl phosphotriester VIII was obtained in good yield upon treatment with diethyl chlorophosphate and sodium hydride in a mixture of tetrahydrofuran and triethylphosphate. The Boc to protective groups were removed upon treatment with HCl in ethanol to give compound IX quantitatively (T. W. Greene and P. G. M. Wuts, Protective groups in Organic Synthesis, $3^{rd}$ Edition, John Wiley & Sons, Inc. 1999). Then, coupling of the free amino group present on intermediate IX with a variety of synthetic amino acid in the presence of 1-hydroxybenzotriazole (HOBt) and 1-[3-(dimethylamino)propyl]-3-ethylcarbodiimide hydrochloride (EDAC) led to derivative II in good to excellent yields. Finally, addition of trimethylsilyl bromide in dichloromethane (DCM) gave compound III in good to excellent yields.

Scheme 2A
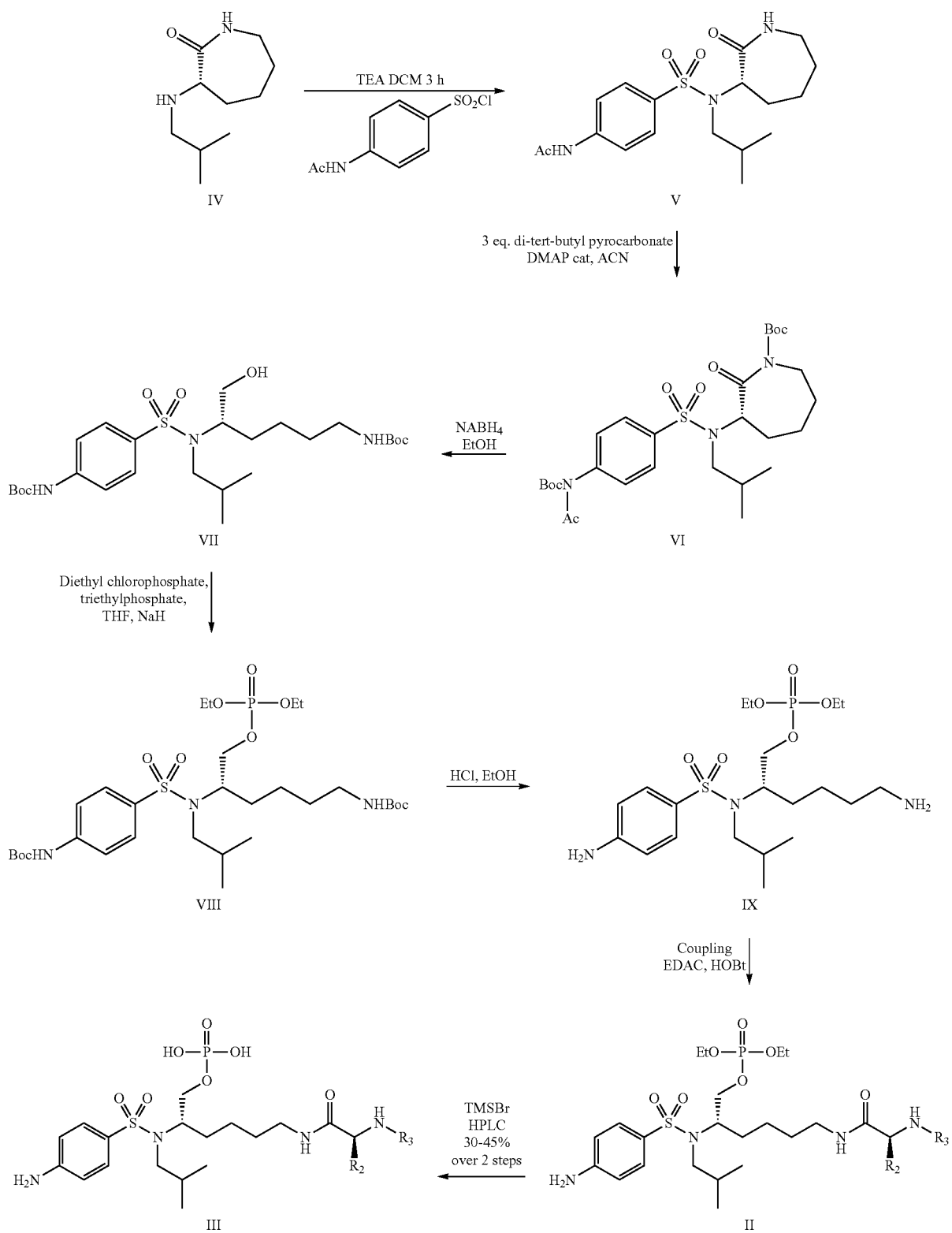
Alternatively, it has also been found that the use of phosphorous oxychloride in the reaction with intermediate III provides, after hydrolysis of the carbamate groups and acylation of the resulting free primary amine, the phosphate mono ester III in only three steps. This improved process yield 50-55% of III (scheme 2B).

From an industrial point of view, the sequence offers an advantageously less expensive, less complex and shorter process for the preparation of III and uses chemicals that are less harmful to the environment.

conditions as reported by Anderson et al. in the *J. Am. Chem. Soc.* 1964, 1839 and afforded compound III in good yield. The use of methyl tert-butyl ketone solvent may facilitate the direct extraction of this intermediate in the aqueous phase.

Scheme 2B

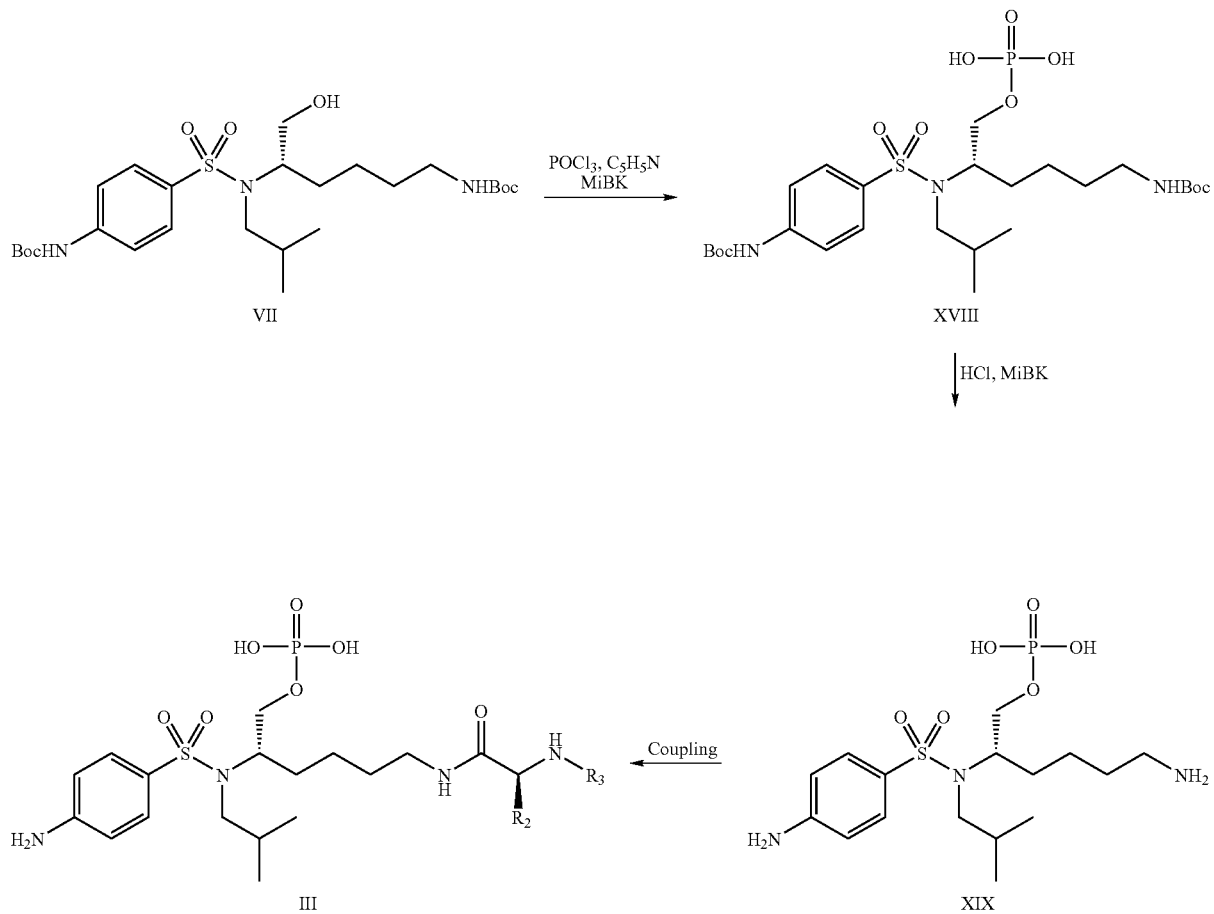

Phosphorylation of VII was carried out with phosphorous oxychloride in the presence of a base, typically an organic base such as pyridine, in a dipolar aprotic solvent such as methyl iso-butyl ketone or acetone. The compound XVIII, was recovered in a yield ranging from 70 to 80%.

Hydrolysis of the carbamate protecting group, carried out, for example, in methyl iso-butyl ketone at 50° C. or in methyl tert-butyl ketone at 55° C. in the presence of concentrated hydrochloric acid, gives the water soluble hydrochloric salt of phosphate mono ester XIX in good to excellent yield. Acylation of XIX with an amino acid was performed under aqueous The pH controlled aqueous solution above may, for example, be treated with 2-methoxycarbonylamino-3,3-diphenyl-propionic acid 2,5-dioxo-pyrrolidin-1-yl ester. Compound PL-461 free acid may be precipitated from reaction mixture by acidification with diluted aqueous hydrochloric acid. Finally, PL-461 (Na)$_2$ may be obtained by recrystallization of crude PL-461 free acid in 1% aqueous sodium chloride solution at pH 9-10 (81% yield).

Scheme 2C presents the synthesis of a specific compound; (1-{5-[4-Amino-benzenesulfonyl)-isobutyl-amino]-6-phosphonooxy-hexylcarbamoyl}-2,2-diphenyl-ethyl)-carbamic acid methyl ester (IIIB: PL-461) based on the general synthesis presented in Scheme 2B.

Scheme 2C.
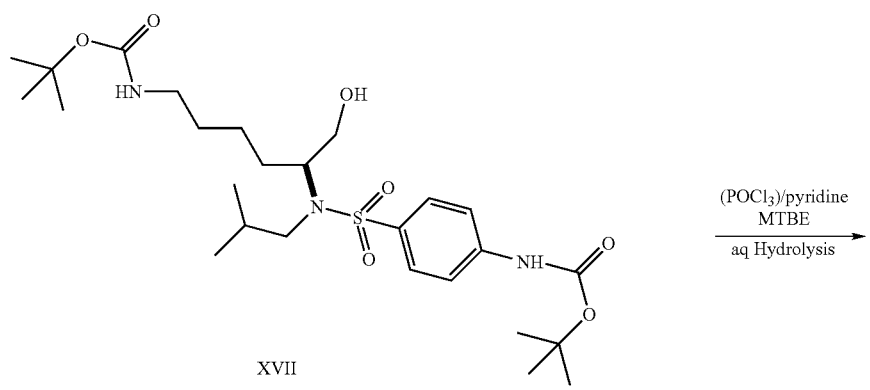
XVII
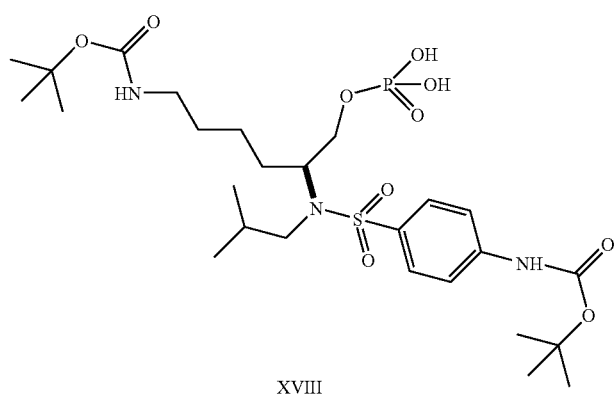
XVIII
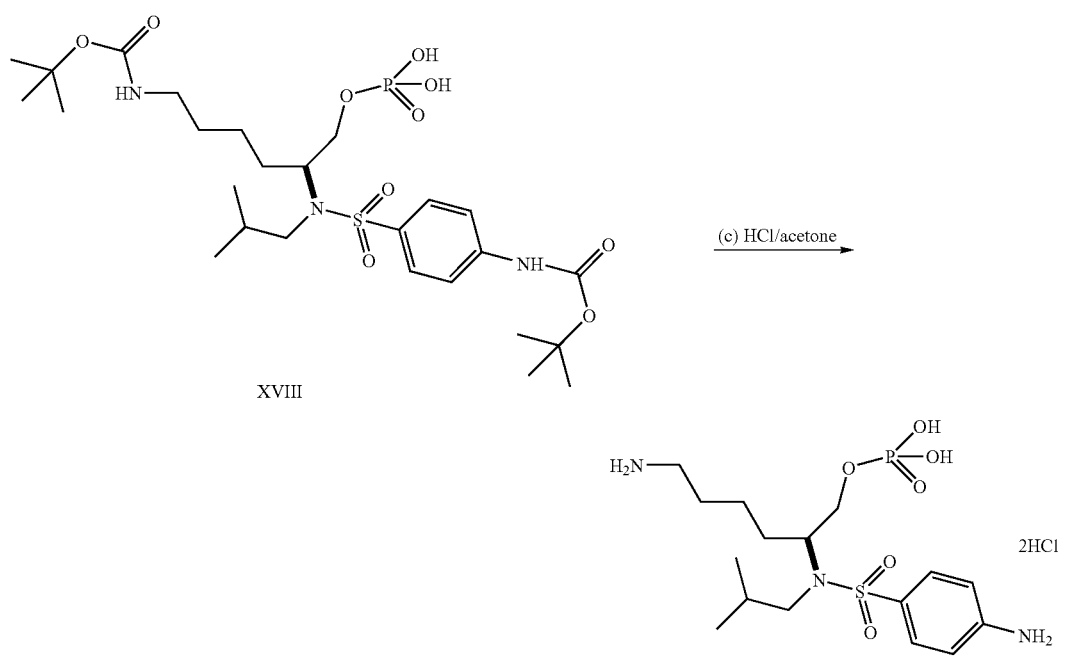
XVIII
XIX
A.
B.

-continued

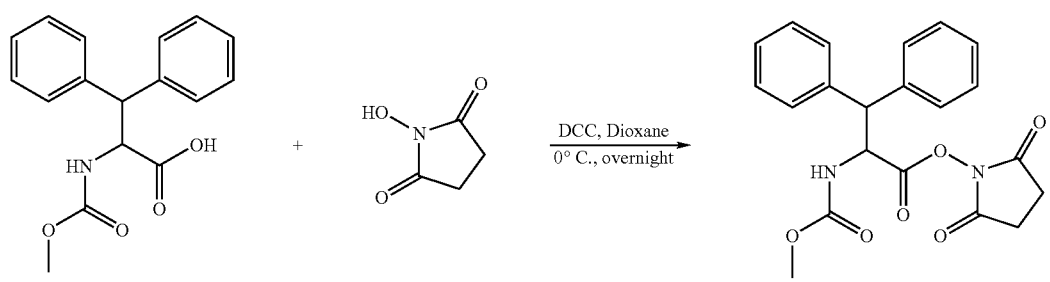

C.

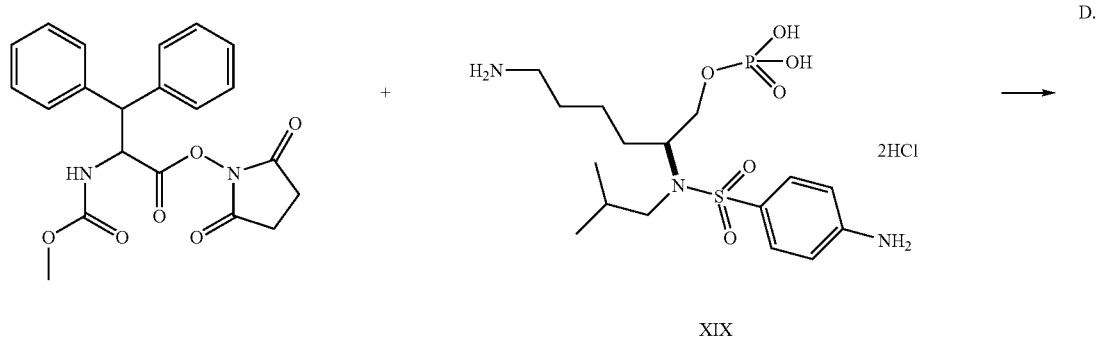

D.

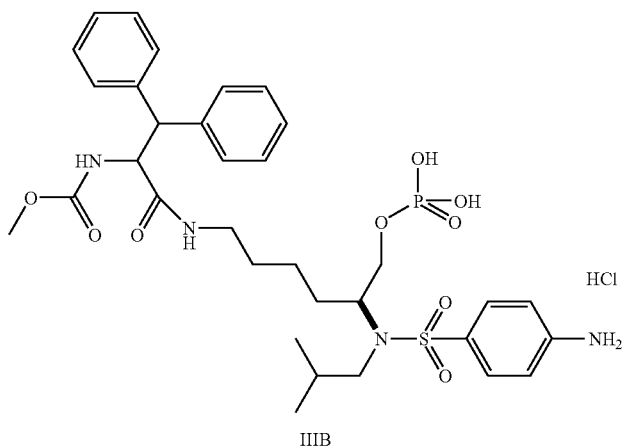

IIIB

Scheme 2D presents the use of an intermediate compound of formula XV in the synthesis of lysine based compounds described herein.

Scheme 2D

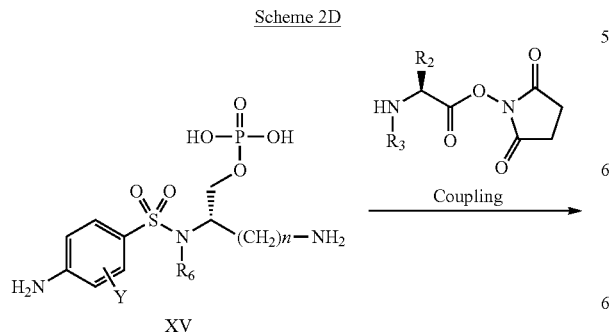

-continued

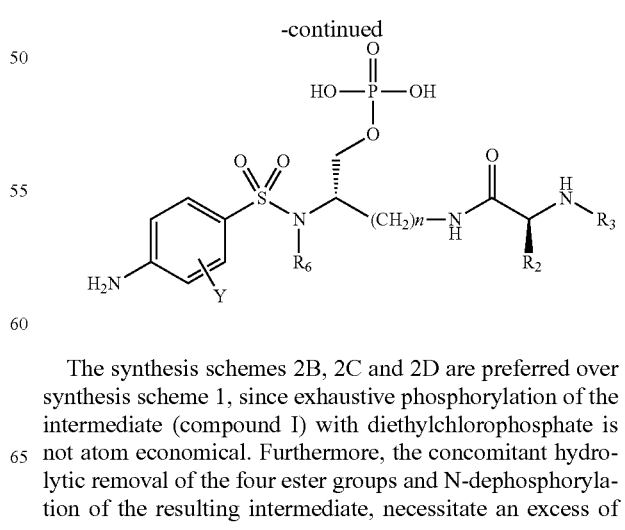

The synthesis schemes 2B, 2C and 2D are preferred over synthesis scheme 1, since exhaustive phosphorylation of the intermediate (compound I) with diethylchlorophosphate is not atom economical. Furthermore, the concomitant hydrolytic removal of the four ester groups and N-dephosphorylation of the resulting intermediate, necessitate an excess of corrosive and hazardous bromotrimethylsilane (up to 4 L per kg of product treated) in large volume of dichloromethane. As a consequence, isolation and purification of this intermediate is technically complex.

Scheme 3 presents the transformation of a diphenylmethyl derivative; (1S,5S)-(1-{5-[(4-amino-benzenesulfonyl)-isobutyl-amino]-6-hydroxy-hexylcarbamoyl}-2,2-diphenyl-ethyl)-carbamic acid methyl ester (PL-100) into its fluorinated phosphate monoester sodium salt analog XI. This reaction sequence may be used to produce any other similar compounds (compounds) made of unsubstituted (or substituted) diphenylmethyl, 1-naphthyl, 2-naphthyl, biphenyl and 9-anthryl groups described in this invention.

Thus, the treatment of PL-100 with Selectfluor™ in acetonitrile gave derivative X in 38% yield. The introduction of the phosphate monoester group was performed as described previously in scheme 1 and 2A. First, the diethyl phosphotriester intermediate was obtained in good yield upon treatment with diethyl chlorophosphate and sodium hydride in a mixture of tetrahydrofuran and triethylphosphate. Secondly, addition of trimethylsilyl bromide in dichloromethane (DCM) gave the phosphate monoester compound in good to excellent yields. The final product XI was easily obtained upon treatment of the phosphate monoester with a solution of sodium hydroxide with good yields.

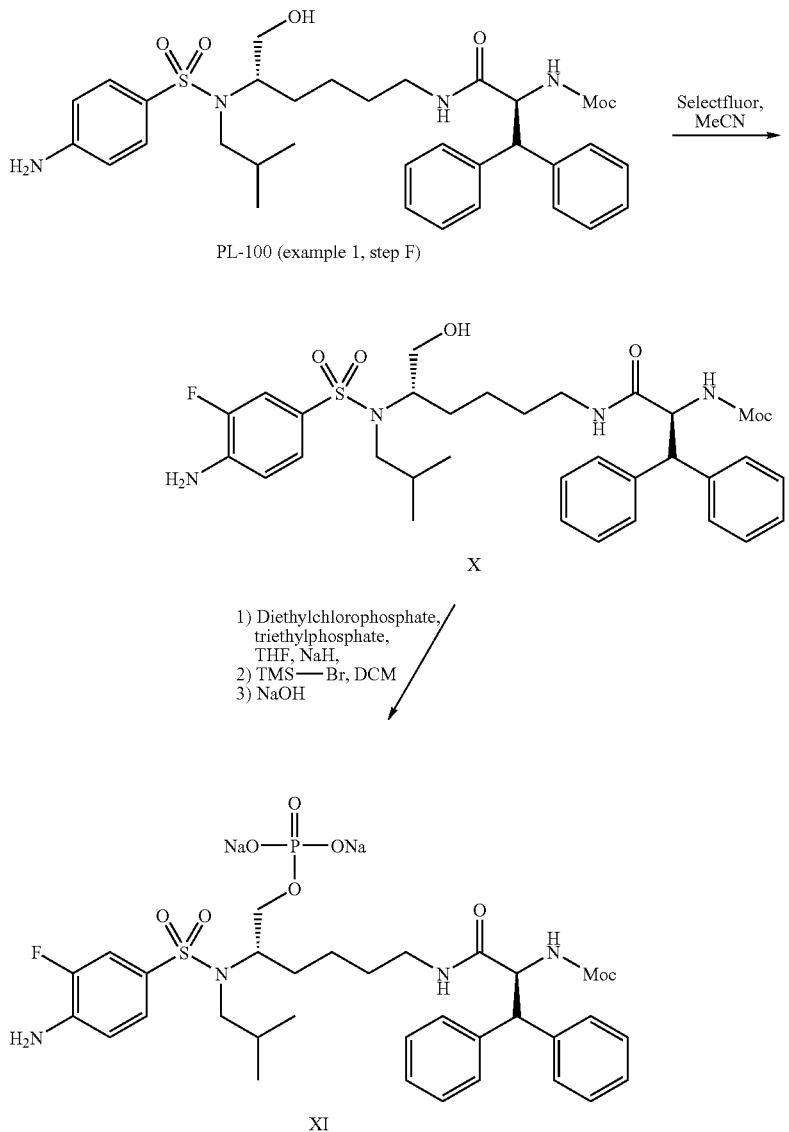

Scheme 4 illustrates a generic example for the transformation of a phosphotriester II into its fluorinated analog XIII in a two-step reaction sequence. This generic example represents a second approach for the synthesis of fluorinated compounds of this invention. In this case, the fluorine atom is added to the phosphotriester II instead of the primary alcohol derivative of general formula I or, more specifically, PL-100 as shown on scheme 3. This alternate reaction sequence may be used to produce any other similar compounds made of unsubstituted (or substituted) diphenylmethyl, 1-naphthyl, 2-naphthyl, biphenyl and 9-anthryl groups described in this invention.

Note:
a) $R_2$ and $R_3$ are as defined herein.

Briefly, treatment of derivative II with Selectfluor™ in acetonitrile gave derivative XII in good yields. Then, addition of trimethylsilyl bromide in dichloromethane (DCM) gave the phosphate monoester compound XIII in good to excellent yields. If desired, the final product XIII may be easily transformed into the phosphate monoester sodium salt analog as described before in scheme 3.

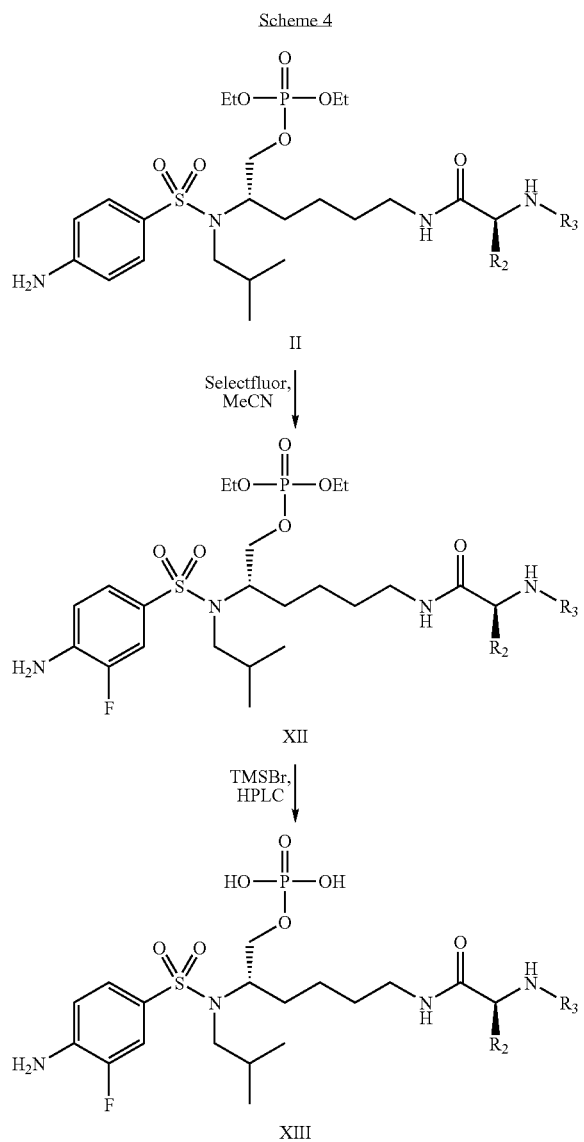

As it may be appreciated by the person skilled in the art, the above synthetic schemes are not intended to be a comprehensive list of all means by which the compound described and claimed in this application may be synthesized but only represent exemplification of synthesis methods among others. Further methods will be evident to those of ordinary skill in the art.

The compounds of this invention may be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

As discussed above, the novel compounds may release the active ingredients that are excellent ligands for aspartyl proteases, for example, HIV-1 protease. Accordingly, these compounds are, by releasing the active ingredient, capable of targeting and inhibiting late stage events in the replication, i.e. the processing of the viral polyproteins by HIV encoded protease. Compounds according to this invention advantageously inhibit the ability of the HIV-1 virus to infect immortalized human T cells over a period of days, as determined by an assay measuring the amount of extracellular p24 antigen; a specific marker of viral replication (see, Meek et al., Nature, 343, pp. 90-92 (1990)).

In addition to their use in the prophylaxis or treatment of HIV or HTLV infection, the compounds according to this invention may also be used as inhibitory or interruptive agents for other viruses which use aspartyl proteases, similar to HIV or HTLV aspartyl proteases, in their life cycle. Such compounds inhibit the proteolytic processing of viral polyprotein precursors by inhibiting aspartyl protease. Because aspartyl protease is essential for the production of mature virions, inhibition of that processing effectively blocks the spread of virus by inhibiting the production and reproduction of infectious virions, particularly from acutely and chronically infected cells. The compounds of this invention advantageously inhibit aspartyl proteases, thus blocking the ability of aspartyl proteases to catalyze the hydrolysis of peptide bonds.

The compounds of this invention may be employed in a conventional manner for the treatment or prevention of HIV, HTLV, and other viral infections, which involve aspartyl proteases for their life (replication) cycle. Such methods of treatment, their dosage levels and requirements may be selected by those of ordinary skill in the art from available methods and techniques. For example, a compound of this invention may be combined with a pharmaceutically acceptable adjuvant for administration to a virally infected patient in a pharmaceutically acceptable manner and in an amount effective to lessen the severity of the viral infection.

Alternatively, the compounds of this invention may be used in vaccines and methods for protecting individuals against viral infection over an extended period of time. The compounds may be employed in such vaccines either alone or together with other compounds of this invention in a manner consistent with the conventional utilization of protease inhibitors or protease inhibitors derivatives in vaccines. For example, a compound of this invention may be combined with pharmaceutically acceptable adjuvants, or delivery systems conventionally employed in vaccines and administered in prophylactically effective amounts to protect individuals over an extended period of time against viral infections, such as HIV infection. As such, the novel compounds of the present invention (upon cleavage of a physiologically cleavable unit) may be administered as agents for treating or preventing viral infections, including HIV infection, in a mammal.

The compounds of this invention may be administered to a healthy or HIV-infected patient (before or after the onset of AIDS symptoms) either as a single agent or in combination with other antiviral agents which interfere with the replication cycle of HIV. By administering the compounds of this invention with other antiviral agents which target different events in the viral life cycle, the therapeutic effect of these compounds is potentiated. For instance, the co-administered antiviral agent may be one which targets early events in the viral life cycle, such as attachment to the cell receptor and cell entry, reverse transcription and viral DNA integration into cellular DNA. Antiviral agents targeting such early life cycle events include among others polysulfated polysaccharides, sT4 (soluble CD4) and other compounds which block binding of virus to CD4 receptors on CD4 bearing T-lymphocytes and other CD4(+) cells, or inhibit fusion of the viral envelope with the cytoplasmic membrane, and didanosine (ddI), zalcitabine (ddC), stavudine (d4T), zidovudine (AZT) and lamivudine (3TC) which inhibit reverse transcription. For example another protease inhibitor may be used with compounds of the present invention. Other anti-retroviral and antiviral drugs may also be co-administered with the compounds of this invention to provide therapeutic treatment for substantially reducing or eliminating viral infectivity and the symptoms associated therewith. Examples of other antiviral agents include ganciclovir, dideoxycytidine, trisodium phosphonoformate, eflornithine, ribavirin, acyclovir, alpha interferon and trimenotrexate. Additionally, other types of drugs may be used to potentiate the effect of the compounds of this invention, such as viral uncoating inhibitors, inhibitors of Tat or Rev trans-activating proteins, antisense molecules or inhibitors of the viral integrase. These compounds may also be co-administered with other inhibitors of HIV aspartyl protease. Furthermore, it may be found useful to administer compounds of the present invention with any other drug (other anti-viral compounds, antibiotics, pain killer, etc.).

Combination therapies according to this invention exert a synergistic effect in inhibiting HIV replication because each component agent of the combination acts on a different site of HIV replication. The use of such combinations also advantageously reduces the dosage of a given conventional anti-retroviral agent that would be required for a desired therapeutic or prophylactic effect as compared to when that agent is administered as a monotherapy. These combinations may reduce or eliminate the side effects of conventional single anti-retroviral agent therapies while not interfering with the anti-retroviral activity of those agents. These combinations reduce the potential of resistance to single agent therapies, while minimizing any associated toxicity. These combinations may also increase the efficacy of the conventional agent without increasing the associated toxicity. Combination therapies encompassed by the present invention include, for example, the administration of a compound of this invention with AZT, 3TC, ddI, ddC, d4T or other reverse transcriptase inhibitors.

Alternatively, the compounds of this invention may also be co-administered with other HIV protease inhibitors such as Ro 31-8959 (Saquinavir; Roche), L-735,524 (Indinavir; Merck), AG-1343 (Nelfinavir; Agouron), A-84538 (Ritonavir; Abbott), ABT-378/r (Lopinavir; Abbott), and VX-478 (Amprenavir; Glaxo) to increase the effect of therapy or prophylaxis against various viral mutants or members of other HIV quasi species.

Administration of compounds of the present invention may be performed, for example, as single agents or in combination with retroviral reverse transcriptase inhibitors, or other HIV aspartyl protease inhibitors. Co-administration of the compounds of this invention with retroviral reverse transcriptase inhibitors or HIV aspartyl protease inhibitors may exert a substantial synergistic effect, thereby preventing, substantially reducing, or completely eliminating viral infectivity and its associated symptoms.

The compounds of the present invention may be administered in such a manner or form which may allow cleavage of the $R_1$ unit to release a protease inhibitor. The compounds of this invention may also be administered, for example, in combination with immunomodulators (e.g., bropirimine, anti-human alpha interferon antibody, IL-2, GM-CSF, methionine enkephalin, interferon alpha, diethyldithiocarbamate sodium, tumor necrosis factor, naltrexone and rEPO) antibiotics (e.g., pentamidine isethionate) or vaccines to prevent or combat infection and disease associated with HIV infection, such as AIDS and ARC.

When the compounds of this invention are administered in combination therapies with other agents, they may be administered sequentially or concurrently to the patient. Alternatively, pharmaceutical or prophylactic compositions according to this invention may be comprised of a combination of one or more compounds of this invention and another therapeutic or prophylactic agent.

Although this invention focuses on the use of the compounds disclosed herein for preventing and treating HIV infection, the compounds of this invention may also be used as inhibitory agents for other viruses that depend on similar aspartyl proteases for obligatory events in their life cycle. These viruses include, but are not limited to, retroviruses causing AIDS-like diseases such as simian immunodeficiency viruses, HIV-2, HTLV-I and HTLV-II. In addition, the compounds of this invention may also be used to inhibit other aspartyl proteases and, in particular, other human aspartyl proteases including renin and aspartyl proteases that process endothelin precursors.

In the description herein, the following abbreviations are used:

Abbreviation Meaning
Ac Acetyl
AcOH Acetic acid
APCI Atmospheric pressure chemical ionization
AIDS Acquired Immunodeficiency Syndrome
AZT 3-Azido-3-deoxythymine (Zidovudine)
Boc Benzyloxycarbonyl
t-Butyl tert-Butyl
CAM Cerium ammonium molybdate
DCM Dichloromethane
DMAP N,N-dimethylaminopyridine
DMSO Dimethylsulfoxide
DMF Dimethylformamide
DNA Deoxyribonucleic acid
EDAC 1-[3-(dimethylamino)propyl]-3-ethylcarbodiimide to hydrochloride
EtOAc Ethyl acetate
EtOH Ethyl alcohol
g Gram
h hour
HIV-1, -2 Human immunodeficiency virus type 1, type 2
HOBt 1-Hydroxybenzotriazole
HPLC High performance liquid chromatography
HTLV-I, -II Human T-cell lymphotrophic virus type I, type II
IL-2 Interleukin-2
Kg Kilogram
L Liter
LC-MS Liquid chromatography-mass spectrometry
M Molar
MeOH Methyl alcohol
mg Milligram
mp Melting point
min Minute
Moc Methoxycarbonyl
mol Mole
mL Milliliter
mmol Millimole
nm Nanometer nM Nanomolar
po Orally
rEPO Recombinant erythropoietin
TLC Thin layer chromatography
3TC 2',3'-Dideoxy-3-thiacytidine
TFA Trifluoroacetic acid
THF Tetrahydrofuran

EXAMPLES

This section describes the synthesis of lysine based compounds able to release an HIV to aspartyl protease inhibitors as described herein. These examples are for the purpose of illustration only and are not to be construed as limiting the scope of the invention in any way. This section presents the detailed synthesis of compounds no. 1 to 10 of this invention.
Materials and Methods Analytical thin layer chromatography (TLC) was carried out with 0.25 mm silica gel E. Merck 60 $F_{254}$ plates and eluted with the indicated solvent systems. Preparative chromatography was performed by flash chromatography, using silica gel 60 (EM Science) with the indicated solvent systems and positive air pressure to allow proper rate of elution. Detection of the compounds was carried out by exposing eluted plates (analytical or preparative) to iodine, UV light and/or treating analytical plates with a 2% solution of p-anisaldehyde in ethanol containing 3% sulfuric acid and 1% acetic acid followed by heating. Alternatively, analytical plates may be treated with a 0.3% ninhydrin solution in ethanol containing 3% acetic acid and/or a CAM solution made of 20 g $(NH_4)_6Mo_7O_{24}$ and 8.3 g $Ce(SO_4)_2$ polyhydrate in water (750 mL) containing concentrated sulfuric acid (90 mL).

Preparative HPLC were performed on a Gilson apparatus equipped with a C18 column, a 215 liquid handler module and 25 mL/min capacity head pumps. The HPLC is operated with a Gilson UniPoint System Software.
Semi-Preparative HPLC Conditions for Purification of Test Compounds:

HPLC system: 2 Gilson #305-25 mL pumps, Gilson #215 liquid handler for injection and collection and a Gilson #155 UV-Vis absorbance detector, all controlled from a Gilson Unipoint V1.91 software
Column: Alltech (#96053) Hyperprep PEP, C-18, 100 Åα, 8 μm, 22×250 min
Flow: 15 mL/min
Solvents: A: $H_2O$; B: $CH_3CN$
Gradient: 25% to 80% of B over 40 min
Detector: absorbance; λ: 210 & 265 nm Crude material dissolved in acetonitrile to a concentration of around 50 to 80 mg/2 mL were injected in each run. Fractions were collected in amounts of 9 mL pertaining absorbance was detected at the UV detector.

Unless otherwise indicated, all starting materials were purchased from a commercial source such as Aldrich Co. or Sigma Co.

Melting points (mp) were determined on a Büchi 530 melting point apparatus in capillary tubes and were uncorrected.

Mass spectra were recorded on a Hewlett Packard LC/MSD 1100 system using APCI or electrospray sources either in negative mode or positive mode.

Nuclear magnetic resonance (NMR) spectra were recorded on a Bruker AMX-II-500 equipped with a reversed or QNP probe. Samples were dissolved in deuterochloroform ($CDCl_3$), deuteroacetone (acetone-$d_6$), deuteromethanol ($CD_3OD$) or deuterodimethylsulfoxide (DMSO-$d_6$) for data acquisition using tetramethylsilane as internal standard. Chemical shifts (*) are expressed in parts per million (ppm), the coupling constants (J) are expressed in hertz (Hz) whereas multiplicities are denoted as s for singlet, d for doublet, 2d for two doublets, dd for doublet of doublets, t for triplet, q for quartet, quint. for quintet, m for multiplet, and br s for broad singlet.

Specific Examples for the Preparation of Derivatives of General Formula I

The following compounds were prepared f using the procedures summarized in schemes 1 to 4.

Example 1A

Preparation of (1S,5S)-(1-(5-[(4-amino-benzene-sulfonyl)-isobutyl-amino]-6-phosphonooxy-hexyl-carbamoyl)-2,2-diphenyl-ethyl)-carbamic acid methyl ester (PL-461)

The preparation of the title compound is based on schemes 1, 2A of this invention.

Step A. Preparation of (3S)-3-isobutylamino-azepan-2-one (IV)

L-α-amino-, -caprolactam (22.0 g) was dissolved in cold dichloroethane (DCM, 200 mL). isobutyraldehyde (12.6 g) was added slowly and stirred until the heat evolved was dissipated (water forms at the surface). The cold solution was added to 46.5 g of powdered $NaBH(OAc)_3$ in DCM (0.5. L). AcOH (70 mL) was added to the solution. The slightly turbid mixture was stirred at 20° C. for 4 h. A 500 mL solution of 2M NaOH was added slowly to the turbid mixture and the pH adjusted to 11 using a concentrated NaOH solution, and then the mixture stirred for a further 20 min. After extraction, the DCM layer was dried with $MgSO_4$, filtered and evaporated. The oil thus obtained crystallizes slowly on standing (27.8 g, 85%) and was used without further purification in the next step.

$^1$H NMR ($CDCl_3$): δ0.93 (d, J=6.5, 3H), 0.97 (d, J=6.5, 3H), 1.39 (t, J=9.8, 1H), 1.47 (m, 1H), 1.78-1.65 (m, 2H), 2.00-1.93 (m, 2H), 2.32-2.2 (m, 2H), 2.38 (t, J=9.7, 1H), 3.16 (m, 3H), 6.62 (s, 1H(NH)). mp 52-54° C. (hexanes).

A small sample was converted to the S-methyl benzyl urea by adding the solid to a solution of S-methyl benzyl isocyanate in MeCN. NMR gives 98% enantiomeric excess (ee).

Step B. Preparation of Nα-isobutyl-Nα-(4-acetamidobenzenesulfonyl)-L-α-amino-, -caprolactam (V)

Nα-isobutyl-L-α-amino-, -caprolactam (IV) (4.1 g free base) was dissolved in DCM (200 mL) and treated with 4.0 g triethylamine, followed by 4-acetamidobenzenesulfonyl chloride (5.2 g). A 0.1 g portion of dimethylaminopyridine was added and the mixture was stirred 5 h. The resulting thick slurry was poured into 500 mL 0.5 M HCl and shaken vigorously. The solid in the biphasic solution was filtered out and washed with cold acetone to give 7.3 g (87%) of clean product.

$^1$H NMR (DMSO-$d_6$): * 0.93 (d, J=6.0, 3H), 0.96 (d, J=6.0, 3H), 1.39 (t, J=12.0, 1H), 1.85-1.65 (m, 3H), 2.08-2.18 (m and s, 6H), 2.90-2.97 (m, 1H), 3.00-3.06 (m, 2H), 3.35 (dd, J=14.2, 8.5, 1H), 4.65 (d, J=8.7, 1H), 6.3 (s, 1H), 7.42 (d, J=8.8, 2H), 7.6 (d, J=8.8, 2H). mp 230-233° C. (EtOH).

Step C. Preparation of (3S)-3-{[4-(acetyl-tert-butoxycarbonyl-amino)-benzenesulfonyl]-isobutyl-amino}-2-oxo-azepane-1-carboxylic acid tert-butyl ester (Boc activation) (VI)

4.2 g of Nα-isobutyl-Nα-(4-acetamidobenzenesulfonyl)-L-α-amino-, -caprolactam (V) was suspended in 30 mL MeCN and briefly sonicated to break up any large chunks. To this white suspension was added 6.7 g (3 eq.) of di-tert-butyl pyrocarbonate in 10 mL MeCN. The suspension was stirred with a magnetic bar and a 120 mg portion of DMAP was added. The solution becomes a clear light yellow after a few minutes. TLC (EtOAc) reveals 1 product Rf 0.9 (starting material Rf at 0.4). The solution is poured in distilled water 20 mL and extracted with ether, dried with $Na_2SO_4$ and evaporated yielding 6.90 g. A sample was recrystallized from hexanes.

$^1$H NMR (DMSO-$d_6$): * 0.68 (d, J=6.0, 3H), 0.85 (d, J=6.0, 3H), 1.39 (s, 10H), 1.47 (s, 9H), 1.85-1.65 (m, 3H), 2.15 (s, 3H), 2.80 (q, J=4, 1H), 3.10-3.36 (m, 2H), 4.01 (d, J=8.0, 1H), 4.85 (d, J=8.7, 1H), 7.32 (d, J=8.8, 2H), 7.87 (d, J=8.8, 2H). mp 123-124° C.

Step D. Preparation of (1S)-4-amino-N-(5-amino-1-hydroxymethyl-pentyl)-N-isobutyl-benzenesulfonamide (VII-Deprotected) (Reductive Ring Opening and Deprotection)

A 3.0 g portion of (3S)-3-{[4-(acetyl-tert-butoxycarbonyl-amino)-benzenesulfonyl]-isobutyl-amino}-2-oxo-azepane-1-carboxylic acid tert-butyl ester (VI, step C) is dissolved in 40 mL EtOH followed by 750 mg $NaBH_4$. Brief heating with a heat gun gives a clear solution. TLC reveals one streaky spot after 20 min (EtOAc). The solution is concentrated to a paste, poured in 40 mL 1N NaOH and extracted with ethyl acetate, the organic phase dried with $NaSO_4$ and evaporated to give 2.8 g of product intermediate (VII); (1S)-{4-[(5-tert-butoxycarbonylamino-1-hydroxymethyl-pentyl)-isobutyl-sulfamoyl]-phenyl}-carbamic acid tert-butyl ester (VII).

The above product intermediate is dissolved in 5 mL EtOH and 5 mL 12 N HCl is added. Vigorous gas evolution is observed for a few minutes. After 2 h the solution is evaporated and rendered basic with concentrated KOH and extracted with EtOAc yielding 1.75 g of a white powder.

$^1$H NMR (DMSO-$d_6$): * 0.82 (m, 6H), 0.97-1.12 (m, 2H), 1.15-1.30 (m, 3H), 1.57 (m, 1H), 1.84 (m, 1H), 2.40 (t, J=7.8, 2H), 2.75 (m, 1H), 2.85 (m, 1H), 3.21 (m, 1H), 3.44 (d, J=6.4, 2H), 5.92 (br s, 2H), 6.59 (d, J=8.0, 2H), 7.39 (d, J=8.0, 2H).

Step E. Preparation (2S)-2-methoxycarbonylamino-3,3-diphenyl-propionic acid

To a solution of L-diphenylalanine (241 mg, 1.0 mmol) (Peptech Corp.) in 5 mL 1N NaOH and 0.5 mL saturated $Na_2CO_3$ (resulting solution at pH 10) was added methoxycarbonyloxysuccinimide (carbonic acid 2,5-dioxo-pyrrolidin-1-yl ester methyl ester) (180 mg, 1.1 mmol) dissolved in 5 mL. Afterwards, the reaction mixture was stirred at room temperature for 2 h. The alkaline solution was extracted once with ether (10 mL) and the aqueous phase was acidified with 1N HCl. This was extracted twice with 20 mL EtOAc, and the combined organic phases were washed with 50 mL 1N HCl. The organic phase was dried over $Na_2SO_4$, filtered and evaporated to an oil, which solidifies to yields 250 mg (83%) of the desired material. This derivative was used as such in the next step.

Step F. Preparation of (1S,5S)-(1-{5-[(4-amino-benzenesulfonyl)-isobutyl-amino]-6-hydroxy-hexylcarbamoyl}-2,2-diphenyl-ethyl)-carbamic acid methyl ester (PL-100)

The title compound was prepared from (1S)-4-amino-N-(5-amino-1-hydroxymethyl-pentyl)-N-isobutyl-benzenesulfonamide (VII-deprotected) (step D) and (2S)-2-methoxycarbonylamino-3,3-diphenyl-propionic acid (step E) using the coupling procedure with HOBt and EDAC described in example 3 (step D). The final product was obtained in 67% yield (121 mg).

LC-MS: 625.3 $(M+H)^+$, 95% pure $^1$H NMR (CD$_3$OD): δ 0.71-0.85 (m, 2H), 0.88 (d, J=6.3, 5H), 0.91-0.96 (m, 2H), 1.29-1.34 (m, 1H), 1.41-1.52 (m, 1H) 1.82-1.92 (m, 1H), 2.61-2.68 (m, 1H), 2.81-2.85 (m, 2H), 2.94-3.05 (m, 2H), 3.38-3.40 (t, J=5.0, 1H), 3.50-3.51 (m, 1H), 3.52 (s, 3H), 4.28 (d, J=11.0 1H), 4.87 (d, J=11.0, 1H), 6.69 (d, J=8.0, 2H), 7.15-718 (m, 2H), 7.20-7.31 (m, 6H), 7.33 (d, J=7.9, 2H), 7.47 (d, J=7.5, 1H).

$^{13}$C NMR (CD$_3$OD): δ 20.0, 20.1, 23.3, 25.4, 28.1, 28.5, 28.9, 38.1, 40.0, 51.2, 51.6, 53.1, 57.2, 57.4, 59.5, 61.9, 62.4, 112.6, 125.7, 126.2, 126.3, 127.9, 128.1, 128.15, 128.2, 128.4, 128.7, 141.3, 141.9, 152.4, 155.9, 169.9, 172.5.

Step G. Preparation of (1S,5S)-{1-[5-[(4-amino-benzenesulfonyl)-isobutyl-amino]-6-(diethoxy-phosphoryloxy)-hexylcarbamoyl]-2,2-diphenyl-ethyl}-carbamic acid methyl ester The PL-100 compound (product of step F, 203 mg, 0.325 mmol) was dissolved in dry tetrahydrofuran (3 mL) and 0.2 mL triethylphosphate under $N_2$ atmosphere. The mixture was stirred at this temperature for 15 min, followed by the addition of diethyl chlorophosphate (0.061 mL, 0.423 mmol). Sodium hydride (60% in mineral oil) (17 mg, 0.423 mmol) was added at 0° C. The solution was stirred for 1 h at 0° C. and 12 h at room temperature. 20 mL of Amberlite XAD-2 was added to the solution and the beads were thoroughly mixed with the solvent. To the mixture was added ice water 0.2 mL, and the THF evaporated off. The beads were then washed with distilled water 6 times 100 mL then extracted three times with ethyl acetate (30 mL). The combined phase was evaporated and the residue was dried under high vacuum. The crude product was purified by flash chromatography using ethyl acetate/hexane (8/2), then EtOAc 100% as eluent. The yield of this reaction is 152 mg 61%.

LC-MS: 761.2 $(M+H)^+$, 90% pure $^1$H NMR (CD$_3$OD): δ 0.68-0.75 (m, 1H), 0.75-0.84 (m, 1H), 0.84-1.10 (m, 9H), 1.21-1.50 (m, 8H), 1.88 (m, 1H), 2.58-2.71 (m, 1H), 2.80-2.89 (m, 1H), 2.89-3.08 (m, 2H), 3.49-3.60 (s, 3H), 3.65-3.74 (m, 1H), 3.85-3.95 (m, 1H), 3.97-4.02 (m, 1H), 4.07-4.21 (m, 4H), 4.29 (d, J=10.8, 1H), 6.71 (d, J=8.0, 2H), 7.10-7.20 (m, 2H), 7.20-7.32 (m, 5M, 7.32-7.45 (m, 3H), 7.50 (d, J=7.5, 2H), 7.86 (br s, 1H).

$^{31}$P NMR (CD$_3$OD): δ 1.62

Step H. Preparation of (1S,5S)-(1-{5-[(4-amino-benzenesulfonyl)-isobutyl-amino]-6-phosphonooxy-hexylcarbamoyl}-2,2-diphenyl-ethyl)-carbamic acid methyl ester (PL-461)

The product of step G prepared above (152 mg) was dissolved in anhydrous dichloromethane (3.0 mL). Trimethylsilyl bromide (0.5 mL) was added at 0° C. The mixture was stirred during 1 h at this temperature and overnight at room temperature. The solvent was evaporated and 0.2 mL water was added to the residue. 3 mL EtOH was added mixed and evaporated. This step was repeated three times and the residue dried in vacuo. Yields 98 mg 70% of the title derivatives of this first example.

LC-MS: 705.2 (M+H)$^+$, 95% pure $^1$H NMR (CD$_3$OD): δ 0.65-0.73 (m, 1H), 0.75-0.83 (m, 1H), 0.89 (d, J=5.6, 8H), 1.27-1.38, (m, 1H), 1.42-4.55 (m, 1H), 1.82-1.94 (m, 1H), 2.57-2.68 (m, 1H), 2.78-2.90 (m, 1H), 2.91-3.09 (m, 2H), 3.54 (s, 3H), 3.60-3.72 (m, 1H), 3.87-4.05 (m, 1H), 4.00 (m, 1H), 4.29 (d, J=11.3, 1H), 4.90 (d, J=11.4, 1H), 6.73 (d, J=8.0, 2H), 7.13-7.22 (m, 2H), 7.22-7.33 (m, 6H), 7.33-7.45 (m, 2H), 7.51 (d, J=7.5, 2H).

$^{31}$P NMR (CD$_3$OD): δ 2.80

Example 1B

Alternative preparation of (1S,5S)-(1-{5-[(4-amino-benzenesulfonyl)-isobutyl-amino]-6-phosphonooxy-hexylcarbamoyl}-2,2-diphenyl-ethyl)-carbamic acid methyl ester (PL-461)

The procedures used for these processes are summarized in schemes 2B-2D.

Step a. Synthesis of {4-[(5-tert-Butoxycarbony-lamino-1-phosphonooxymethyl-pentyl)-isobutyl-sulfamoyl]-phenyl}carbamic acid tert-butyl ester (VIII)

To a cooled solution of VII (17 g, 31 mmol) and pyridine (30 mL, 372 mmol; Aldrich Chemical Company) in 200 mL of methyl iso-butyl ketone (Aldrich Chemical Company) was added dropwise neat phosphorous oxychloride (8.4 mL, 93 mmol; Aldrich Chemical Company). Cooling was removed following the addition and the mixture containing a white precipitate was stirred for 12 hours at room temperature. The solution was then poured into 600 mL of cold (ice bath) aqueous 1N HCl. The biphasic mixture was heated to 50° C. and stirred vigorously for 2 hrs. The cooled mixture was decanted. The aqueous phase was extracted once with methyl iso-butylketone and the combined organic phases were washed with water. The solution was dried over sodium sulfate, filtered and concentrated to a red paste. The intermediate was extracted in aqueous sodium hydroxide (1M). The aqueous phase was washed twice with ethyl acetate, separated and then neutralized with diluted aqueous hydrochloric acid. Extraction with ethyl acetate yielded 13 g to 19 g (88%) of the title compound. (LC-MS: m/z 624.2; $^1$H NMR (acetone-d$_6$) δ: 7.8 (dd, 4H), 4.1-3.95 (m, 3H), 3.05 (m, 1H), 2.95 (m, 3H), 1.95 (m, 1H), 1.73 (m, 4H), 1.5 (s, 9H), 1.455 (s, 9H), 1.15 (m, 2H), 0.89 (m, 6H). The enantiomeric purity of intermediate XVIII may be determined by deriving the pendant alcohol using MOCDIP, through a DCC/DMAP condensation, then determining the ee either qualitatively with a TLC or quantitatively through HPLC.

Step b. Synthesis of the aqueous solution of the bis-hydrochloride salt of phosphoric acid mono-{6-amino-2-[(4-amino-benzenesulfonyl)-isobutyl-amino]-hexyl}ester (XIX)

To a solution of XVIII (19 g, 31 mmol) in 150 mL of methyl iso-butyl ketone was added 7.2 ml (90 mmol) of concentrated HCl and the resulting mixture heated to 55° C. for 6 hours then allowed to cool to room temperature. Water (50 mL) was added and the resulting two phase mixture separated to give approximately a 0.6 M aqueous solution of XIX.

MS: m/z 424.2; $^1$H NMR (CD$_3$OD) δ 7.95 (d, 2H), 7.35 (d, 2H), 3.90-3.05 (m, 3H), 2.9 (s, 4H), 1.95 (m, 1H), 1.65 (m, 4H), 1.45 (m, 2H), 0.9 (m, 6H).

Alternatively, in a 1-L, one-necked, round bottom flask that contain a magnetic stirring bar are placed 19 g (31 mmol) of {4-[(5-tert-Butoxycarbonylamino-1-phosphono-oxymethyl-pentyl)-isobutyl-sulfamoyl]-phenyl}-carbamic acid test-butyl ester (XVIII), 150 mL of acetone and 7.2 ml (90 mmol) of concentrated HCl. The flask is fitted with a condenser and the solution is refluxed for 6 hrs. The reaction was monitored by LC-MS. The solvent is evaporated using a rotary evaporator and the gummy red residue is partitioned between 100 mL of ethyl acetate and 50 mL of water. The crude brown aqueous solution of the amine.2HCl (2×32.5 mL) is recovered in 50 mL polypropylene tubes and used as is without further purification.

Step c. Synthesis of (1-{5-[(4-Amino-benzenesulfonyl)-isobutyl-amino]-6-phosphonooxy-hexylcarbamoyl}-2,2-diphenyl-ethyl)carbamic acid methyl ester (IIIB: PL-461)

57 mL (or approximately 26 mmol) of the aqueous solution of phosphoric acid mono-{6-amino-2-[(4-amino-benzenesulfonyl)-isobutyl-amino]-hexyl}ester (XIX) was neutralized with 40 mL of 1N sodium hydroxide. The pH of the solution (pH-4-5) was then adjusted to pH=8 by adding 150 mL solution of saturated of sodium bicarbonate. To this well stirred solution was added a freshly prepared solution, in 130 mL of acetone, of methoxycarbonylamino-3,3-diphenyl-propionic acid 2,5-dioxo-pyrrolidin-1-yl ester (13.34 g, 34 mmol) prepared according to Anderson et al *J. Am. Chem. Soc.* 1964, 1839. The resulting clear solution was stirred for 12 h. The reaction mixture was concentrated and the remaining aqueous phase extracted twice with ethyl acetate. The aqueous phase was then acidified with 1N hydrochloric acid and the resulting suspension extracted with ethyl acetate. The organic phase was washed with water then dried over sodium sulfate, filtered and concentrated on a rotary evaporator. The solid residue was again suspended in ethyl acetate and acidified with HCl (g). The resulting beige precipitate was collected by filtration to give 12.5 g (66%) of the title product. Purity was determined by LC_MS and is greater than 97%.

MS: m/z 705.2; $^1$H NMR (CD$_3$OD) δ 7.52 (d, 2H), 7.37 (d, 2H), 7.30-7.19 (m, 8H), 6.69 (d, 2H), 4.92 (d, 1H), 4.28 (d, 1H), 3.87 (m, 1H), 3.76 (m, 1H), 3.67 (m, 1H), 3.54 (s, 3H), 3.04 (m, 2H), 2.85 (m, 2H), 2.65 (m, 2H), 1.94 (m, 1H), 1.65 (m, 1H), 1.25 (m, 1H), 0.92-0.88 (m, 10H).

In step c. above, methoxycarbonylamino-3,3-diphenyl-propionic acid 2,5-dioxo-pyrrolidin-1-yl ester may be prepared as follow; In a 500 mL, erlenmeyer flask is placed 26 g (87 mmol) of MOCDIP 175 mL of anhydrous dioxane and 10 g (87 mmol) of N-hydroxysuccimide. The solution is cooled in an ice bath while 18 g (87 mmol) of DCC is added. The mixture is allowed to stand in the refrigerator at (~0)° C. overnight. The formed dicyclohexylurea is filtered and washed with dioxane. The filtrate is concentrated using a rotary evaporator to yield a solid that is triturated in ether. The white solid is recovered by filtration and dried. The yield is 35 g.

Example 2

Preparation of (1S,5S)-(1-{5-[(4-amino-benzenesulfonyl)-isobutyl-amino]-6-phosphonooxy-hexylcarbamoyl}-2,2-diphenyl-ethyl)-carbamic acid methyl ester sodium salt (PL-462)

70.7 mg of the final product of either examples 1A or 1B is added to 1 mL 0.1 N NaOH and diluted with 1 mL of distilled water. The Solution is then frozen and lyophilized. Yields 67.2 mg (92%) of the desired material with 95% purity.

$^1$H NMR (CD$_3$OD): δ 0.72-0.83 (m, 1H), 0.90 (d, J=5.8, 9H), 1.26-1.38 (m, 1H), 1.53-1.65 (m, 1H), 1.88-2.00 (m, 1H), 2.60-2.70 (m, 1H), 2.79-2.89 (m, 1H), 2.98-3.00 (m, 1H), 3.00-3.08 (m, 1H), 3.54 (s, 3H), 3.58-3.71 (m, 1H), 3.72-3.83 (m, 1H), 3.84-3.95 (m, 1H), 4.28 (d, J=11.1, 1H), 4.91 (d, J=11.0, 1H), 6.70 (d, J=7.6, 2H), 7.12-7.22 (m, 2H), 7.22-7.32 (m, 6H), 7.33-7.40 (m, 2H), 7.50 (d, J=7.7, 2H).

$^{31}$P NMR (CD$_3$OD): δ 3.13

Crystals of the PL-462 compound were obtained as follows. Ten grams (10.00 g) of PL-461 (14.2 mmol) was weighed out. Thirty milliliters (30 mL) of 1% NaCl was then placed in a beaker and the PL-461 powder added in 1 g portions. After each portion the pH was adjusted with NaOH 40% to pH 6-8. In the last few portions heat was applied with a heat gun to help in the dissolution of the slightly turbid, honey coloured solution. The temperature did not exceed 60° C. A Further 15 mL of distilled water was added bringing the total volume to 50 mL. Final concentration gave 200 mg/mL pH adjusted to 8.5-10 (pH paper). After cooling at room temperature for 3 h a thick paste was obtained. This paste was filtered and pressed to give an off-white cake (24 g wet weight).

About 35 mL of the liquour was recovered and re-acidified to recover the PL-461 (get 1.6 g) from the discards. The cake was re-dissolved in 40 mL of distilled water with warming to 50° C. and left to cool for 5 h. The resulting thick paste was filtered and pressed. The resulting solid was then dried in a lyophilizer for 36 h. The yield for PL-462 was 8.89 g, 11.8 mmol (83%).

HPLC analysis showed identical profile of PL-462 as the free acid (PL-461) and 93-94% unit equivalence. A microscopic image (200×) of the PL-462 crystal in solution is shown in FIG. 1.

Figure 2:
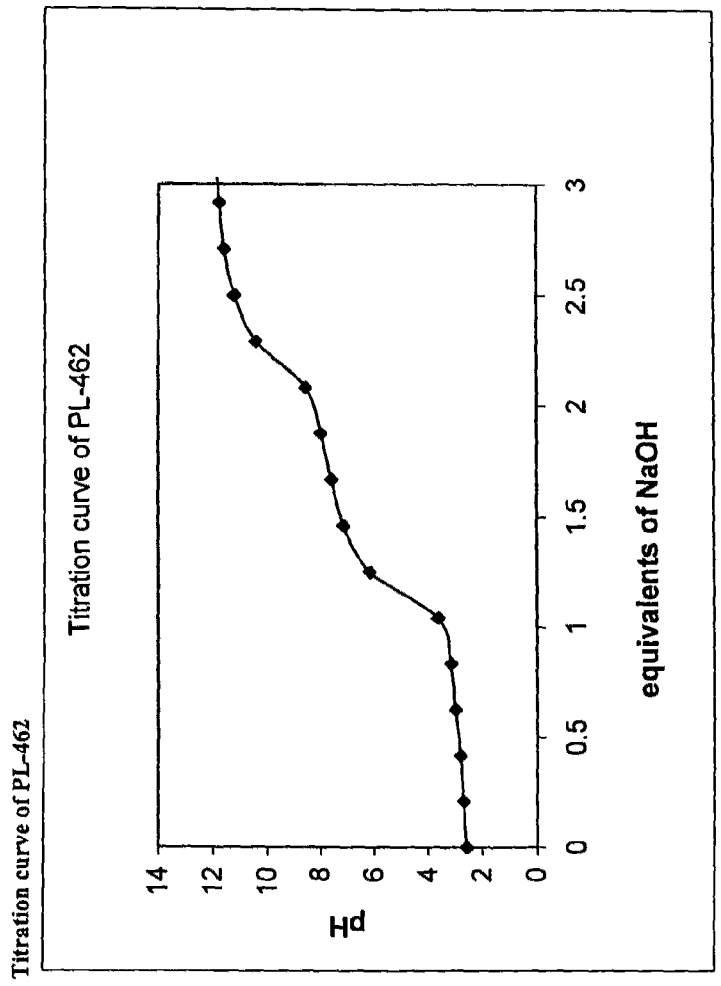
FIG. 2 is a diagram representing the titration curve of PL-462 with NaOH.

Forty (40) mg (0.05) mmol of PL-461 was dissolved in 10 mL 50% dioxane solution with magnetic stirring and the pH measured with a pH Meter. A solution of standardized 0.01 N NaOH was placed in a burette and dispensed portionwise with concomitant pH readings shortly after each aliquot. A graph of pH vs volume of NaOH was plotted and is shown in FIG. 2.

Example 3

Preparation of (1S,5S)-(1-{5-[(4-amino-benzenesulfonyl)-isobutyl-amino]-6-phosphonooxy-hexyl-carbamoyl}-2-naphthalen-2-yl-ethyl)-carbamic acid methyl ester (PL-507)

The preparation of the title compound is based on scheme 2A of this invention.

Step A. Preparation of (1S)-(4-{[5-tert-butoxycarbonylamino-1-(diethoxyphosphoryloxymethyl)-pentyl] isobutyl-sulfamoyl}-phenyl)-carbamic acid tert-butyl ester (VIII)

2.00 g (3.7 mmol) (1S)-{4[(5-tert-butoxycarbonylamino-1-hydroxymethyl-pentyl)-isobutyl-sulfamoyl]-phenyl}-carbamic acid tert-butyl ester (VII) (example 1A, step D) is dissolved in 0.63 mL triethylphosphate and 10 mL THF at 0° C. under inert argon atmosphere. 0.63 mL (4.44 mmol) diethylchlorophosphate is added and then 0.25 g (6.2 mmol), NaH 60% in oil is added in portionwise. The mixture is allowed to warm to room temperature and left to stir for 2 h (LC-MS showed completion after 1 h). To the solution is added 20 mL of Amberlite XAD-2 resin and the slurry thoroughly mixed and added to 200 mL ice water. After stirring for 15 min. the resin suspension is filtered and the resin washed several times with distilled water (500 mL). The desired product is desorbed from the resin with acetone (5×50 mL), EtOAc (5×50 mL), the organic phase is then dried over Na$_2$SO$_4$. After evaporation of the solvent 2.66 g (89%) of clear oil is obtained. The crude product contains a fraction with two diethyl phosphates and is used as is in the next step.

$^1$H NMR (CD$_3$OD): δ 0.91 (d, J=6.3, 6H), 1.11-1.21 (m, 2H), 1.33 (t, J=6.9, 10H), 1.43 (s, 9H), 1.53 (s, 10H), 1.90-1.97 (m, 1H), 2.88-2.96 (m, 3H), 2.96-3.04 (m, 1H), 3.81-3.90 (m, 1H), 3.91-3.99 (m, 1H), 4.01-4.14 (m, 4H), 7.61 (d, J=8.3, 2H), 7.72 (d, J=8.4, 2H).

$^{31}$P NMR (CD$_3$OD): δ 1.59

Step B. Preparation of (2S)-phosphoric acid 6-amino-2-[(4-amino-benzenesulfonyl)-isobutyl-amino]-hexyl ester diethyl ester (IX)

The crude product obtained in the previous step (VIII, 2.66 g) is dissolved in 12 mL EtOH. 4 mL of HCl$_{conc.}$ is added and heated briefly to 70° C. then left at room temperature for 3 h. The solvent is evacuated and the residue triturated with 50 mL ether. The thick residue is then dissolved in 3 mL ice water and the pH adjusted to 12 with 50% NaOH. The thick slurry obtained is extracted with EtOAc (3×50 mL) and the organic phase dried over Na$_2$SO$_4$. After filtration of the drying agent the organic phase is evacuated to yield 1.84 g (98%) of the desired product (IX).

LC-MS: 480.2 (M+H)$^+$, 95% pure.

$^1$H NMR (CD$_3$OD): δ 0.91 (s, 6H), 1.11-1.26 (m, 3H), 1.28-1.43 (m, 8H), 1.45-1.51 (m, 1H), 1.52-1.61 (m, 1H), 1.89-1.96 (m, 1H), 2.56 (t, J=6.7, 2H), 2.85-2.91 (m, 1H), 2.98-3.11 (m, 1H), 3.79-3.99 (m, 1H), 3.94 (d, J=5.3, 1H), 4.09-4.11 (m, 4H), 6.69 (d, J=7.9, 2H), 7.50 (d, J=7.9, 2H).

$^{31}$P NMR (CD$_3$OD): δ 1.61

Step C. Preparation of (2S)-2-methoxycarbonylamino-3-naphthalen-2-yl-propionic acid (or L-Moc-2-naphthylalanine)

To a solution of L-2-naphthylalanine (215 mg, 1 mmol) (Peptech Corp.) in 5 mL 1N NaOH and 0.5 mL saturated Na$_2$CO$_3$ (resulting solution at pH 10) was added methoxycarbonyloxysuccinimide (187 mg, 1.1 mmol) dissolved in 5 mL. Afterwards, the reaction mixture was stirred at room temperature for 2 h. The alkaline solution was extracted once with ether (10 mL) and the aqueous phase was acidified with 1N HCl. This was extracted twice with 20 mL EtOAc, and the combined organic phases were washed with 50 mL 1N HCl. The organic phase was dried over Na$_2$SO$_4$, filtered and evaporated to an oil, which solidifies to yields 200 mg (73%) of the desired material. This intermediate (referred as the N-substituted amino acid) was used without further purification in the next step.

Step D. Preparation of (1S,5S)-(1-{5-[(4-amino-benzenesulfonyl)-isobutyl-amino]-6-phosphonooxy-hexylcarbamoyl}-2-naphthalen-2-yl-ethyl)-carbamic acid methylester (PL-507)

100 mg L-Moc-2-naphthylalanine (step C) was activated with 100 mg EDAC and 57 mg HOBt in 1.5 mL DMF for 30 minutes. Then, 100 mg of phosphoric acid 6-amino-2-[(4-amino-benzenesulfonyl-isobutyl-amino]-hexyl ester diethyl ester (step B) was added and left to stir at room temperature for 1 h. 40 mL of 1M $K_2CO_3$ was added to the DMF solution and left for 10 min. 50 mL of EtOAc was then added and the mixture was then agitated vigorously. Separation of the EtOAc phase was effected, followed by extraction with 5% citric acid (50 mL) once, then water (50 mL) 3 times and finally brine. The organic phase was the separated and evaporated. The residue was taken up in 50 mL DCM and re-evaporated. The residue was again taken up in 50 mL DCM and 0.5 mL of TMSBr was added. The solution was left overnight (16 h). The DCM was evacuated and a solution of ice cold MeOH:Water 1:1 was added, stirred briefly and evacuated. The residue was triturated with ether then dissolved in 1N NaOH. The clear solution was extracted with ether and the aqueous phase acidified with 6N HCl. The white precipitated was then collected by filtration and dried in vacuo overnight. Yields 88 mg of the title compound.

LC-MS: 679.8 (M+H)$^+$, 95% pure.

$^1$H NMR (CD$_3$OD): δ 0.89-0.98 (m, 8H), 1.15 (m, 2H), 1.35 (m, 1H), 1.45 (m, 1H), 1.88 (m, 1H), 2.84 (m, 2H), 2.98 (m, 1H), 3.01 (m, 2H), 3.24 (m, 1H), 3.56 (s, 3H), 3.60 (m, 1H), 3.81 (m, 1H), 3.99 (m, 1H), 4.39 (t, J=6.8, 1H), 6.91 (d, J=8.0, 2H), 7.34 (d, J=8.0, 1H), 7.45 (m, 2H), 7.58 (d, J=8.0, 2H), 7.66 (s, 1H), 7.70-7.82 (m, 3H).

$^{31}$P NMR (CD$_3$OD): δ 2.56

Example 4

Preparation of (2S,2S) phosphoric acid mono-(2-[(4-amino-benzenesulfonyl)-isobutyl-amino]-6-(2-[(morpholine-4-carbonyl)-amino]-3-naphthalen-1-yl-propionylamino)-hexyl) ester (PL-498)

Step A. Preparation of (2S)-2-[(morpholine-4-carbonyl)-amino]-3-naphthalen-1-yl-propionic acid To a solution of L-1-naphthylalanine (215 mg, 1 mmol) (Peptech Corp.) in 5 mL 1N NaOH and 0.5 mL saturated Na$_2$CO$_3$ (resulting solution at pH 10) was added morpholine-4-carbonyl chloride (150 mg, 1.0 mmol) dissolved in 5 mL. Afterwards, the reaction mixture was stirred at room temperature for 2 h. The alkaline solution was extracted once with ether (10 mL) and the aqueous phase was acidified with 1N HCl. This was extracted twice with 20 mL EtOAc, and the combined organic phases were washed with 50 mL 1N HCl. The organic phase was dried over Na$_2$SO$_4$, filtered and evaporated to an oil, which solidifies to yields 125 mg (38%) of the desired material. This compound was used as such in the next step.

Step B. Preparation of (2S,2S) Phosphoric acid mono-(2-[(4-amino-benzenesulfonyl)-isobutyl-amino]-6-{2-[(morpholine-4-carbonyl)-amino]-3-naphthalen-1-yl-propionylamino}-hexyl) ester (PL-498)

This compound was made as for the preparation of the product of example 3 (step D) with 100 mg of (2S)-2-[morpholine-4-carbonyl)-amino]-3-naphthalen-1-yl-propionic acid (step A of this example). The resulting precipitated residue was further purified by reverse phase preparative HPLC. Yields 41 mg of the final compound.

LC-MS: 734.8 (M+H)$^+$, 95% pure.

$^1$H NMR (CD$_3$OD): δ 0.83-0.98 (m, 8H), 1.00-1.25 (m, 4H), 1.45-1.52 (m, 1H), 1.52-1.66 (m, 1H), 1.88-1.99 (m, 1H), 2.77-2.92 (m, 2H), 2.98-3.16 (m, 3H), 3.40-3.49 (m, 1H), 3.50-3.56 (m, 6H), 3.67-3.69 (m, 1H), 3.81-3.89 (m, 1H), 3.99-4.05 (m, 1H), 4.59 (t, J=6.0, 1H), 6.75 (d, J=8.0, 2H), 7.30-7.60 (m, 7H), 7.75 (d, J=8.0, 1H), 7.90 (d, J=7.8, 1H), 8.23 (d, J=7.8 2H).

$^{31}$P NMR (CD$_3$OD): δ 2.71

Example 5

Preparation of (2S,2S)-phosphoric acid mono-{6-(2-acetylamino-3,3-diphenyl-propionylamino)-2-[(4-amino-benzenesulfonyl)-isobutyl-amino]-hexyl}ester (PL-504)

Step A. Preparation (2S)-2-acetylamino-3,3-diphenyl-propionic acid

To a solution of L-diphenylalanine (100 mg, 0.4 mmol) (Peptech Corp.) in 5 mL 1N NaOH and 0.5 mL saturated Na$_2$CO$_3$ (resulting solution at pH 10) was added acetyl chloride (0.5 mmol) dissolved in 5 mL. Afterwards, the reaction mixture was stirred at room temperature for 2 h. The alkaline solution was extracted once with ether (10 mL) and the aqueous phase was acidified with 1N HCl. This was extracted twice with 20 mL EtOAc, and the combined organic phases were washed with 50 mL 1N HCl. The organic phase was dried over Na$_2$SO$_4$, filtered and evaporated to an oil, which solidifies to yields 70 mg (60%) of the desired material. This crude intermediate was used as such in the next step.

Step B. Preparation of (2S,2S)-phosphoric acid mono-{6-(2-acetylamino-3,3-diphenyl-propionylamino)-2-[(4-amino-benzenesulfonyl)-isobutyl-amino]-hexyl}ester (PL-504)

This compound was made as for the preparation of the product of example 3 (step D) with 100 mg of (2S)-2-acetylamino-3,3-diphenyl-propionic acid (this example step A). The final product was obtained in 30% yield (30 mg).

LC-MS: 689.3 (M+H)$^+$, 95% pure.

$^1$H NMR (CD$_3$OD): δ 0.77-1.04 (m, 9H), 1.10-1.17 (m, 1H), 1.23-1.49 (m, 1H), 1.46-1.57 (m, 1H), 1.78 (s, 3H), 1.88-1.99 (m, 1H), 2.80-2.92 (m, 2H), 2.92-3.08 (m, 2H), 3.63-3.75 (m, 1H), 3.79-3.95 (m, 1H), 4.00 (m, 1H), 4.34 (d, J=11.3, 1H), 5.19-5.28 (m, 1H), 6.77-6.85 (m, 2H), 7.10-7.20 (m, 2H), 7.27-7.33 (m, 6H), 7.32-7.41 (m, 2H), 7.49-7.62 (m, 2H).

$^{31}$P NMR (CD$_3$OD): δ 2.70

Example 6

Preparation of (1S,5S)-(1-{5-[(4-amino-3-fluoro-benzenesulfonyl)-isobutyl-amino]-6-phosphonooxy-hexylcarbamoyl}-2,2-diphenyl-ethyl)-carbamic acid methyl ester (PL-515)

First Methodology: The Preparation of the Title Compound is Based on Scheme 3 of this Invention.

Step A. Preparation of (1-{5-[(4-amino-3-fluoro-benzenesulfonyl)-isobutyl-amino]-6-hydroxy-hexyl-carbamoyl}-2,2-diphenyl-ethyl)-carbamic acid methyl ester (X) (PL-337)

The product of example 1A, step F (0.624 g, 1 mmol) is dissolved in 5 mL MeCN at 24° C. SelectFluor 0.35 g (1 mmol) is added in one portion and stirred for 1 h. 1 mL of water is added and the solution was injected directly into a preparative reverse-phase HPLC. The product was collected and lyophilized to give 250 mg (38%) yield of a white solid.

LC-MS: 643.3 (M+H)$^+$, 99% pure.

$^1$H NMR (MeOD): δ 0.71-0.85 (m 2H), 0.88 (d, J=6.3, 6H), 0.91-0.96 (m, 2H), 1.21-1.29 (m, 1H), 1.41-1.52 (m, 1H) 1.82-1.92 (m, 1H), 2.61-2.68 (m, 1H), 2.81-2.85 (m, 2H), 2.94-3.05 (m, 2H), 3.38-3.40 (t, J=5, 1H), 3.49-3.52 (m, 5H), 4.28 (d, J=10, 1H), 4.87 (d, J=10, 1H) 6.90 (t, J=8.3, 1H), 7.20 (m, 2H), 7.28 (m, 3H), 7.33 (m, 3H), 7.39 (m, 4H).

Step B. Preparation of (1S,5S)-{1-[5-[(4-amino-3-fluoro-benzenesulfonyl)-isobutyl-amino]-6-(diethoxy-phosphoryloxy)-hexylcarbamoyl]-2,2-diphenyl-ethyl}-carbamic acid methyl ester The product of step A was phosphorylated with chlorodiethylphosphate following the procedure described in example 1A, step G. Yields 157 mg, 68%.

LC-MS: 779.3 (M+H)$^+$, 95% pure.

$^1$H NMR (CD$_3$OD): δ 0.82 (m, 1H), 0.92 (d, J=6.2, 8H), 0.96 (m, 3H), 1.36 (d, J=3.7, 6H), 1.90 (m, 1H), 2.69 (m, 1H), 2.89 (m, 1H), 2.98 (m, 2H), 3.56 (s, 3H), 3.74 (m, 1H), 3.93 (m, 1H), 4.03 (m, 1H), 4.12 (q, J=7.5 and 14.8, 4H), 4.32 (d, J=11.4, 1H), 4.92 (d, J=11.4, 1H), 6.90 (t, J=8.3, 1H), 7.20 (m, 2H), 7.28 (m, 3H), 7.33 (m, 3H), 7.39 (m, 4H).

$^{31}$P NMR (CD$_3$OD): δ 1.65

Step C. Preparation of (1S,5S)-(1-{5-[(4-amino-3-fluoro-benzenesulfonyl)-isobutyl-amino]-6-phosphonooxy-hexylcarbamoyl}-2,2-diphenyl-ethyl)-carbamic acid methyl ester (XI) (PL-515)

Deprotection was effected using the procedure described in example 1A, step G. Yields 101 mg.

LC-MS: 723.2 (M+H)$^+$, 95% pure.

$^1$H NMR (CD$_3$OD): δ 0.65-0.77 (m, 1H), 0.77-0.85 (m, 1H), 0.85-1.05 (m, 9H), 1.25-1.39 (m, 1H), 1.40-1.52 (m, 1H), 1.82-1.98 (m, 1H), 2.58-2.72 (m, 1H), 2.82-2.92 (m, 1H), 2.92-3.05 (m, 2H), 3.54 (s, 3H), 3.64-3.75 (m, 1H), 3.80-3.92 (m, 1H), 3.91-4.04 (m, 1H), 4.29 (d, J=11.4, 1H), 7.19 (t, J=6.6, 1H), 7.13-7.21 (m, 2H), 7.22-7.33 (m, 6H), 7.34-7.38 (m, 2H), 7.39-7.48 (m, 2H).

$^{31}$P NMR (CD$_3$OD): δ 2.74

Second Methodology: The Preparation of the Title Compound is Based on Scheme 4 of this Invention.

Step A. Preparation (1S,5S)-(1-{5-[(4-amino-benzenesulfonyl)-isobutyl-amino]-6-phosphonooxy-hexylcarbamoyl}-2,2-diphenyl-ethyl)-carbamic acid methyl ester (PL-461)

(2S)-2-methoxycarbonylamino-3,3-diphenyl-propionic acid (example 1A, step E) 0.9 g, 3 mmol) was activated in DMF (5 mL) with EDAC (1.7 g, 9 mmol) and HOBt (1.2 g, 9 mmol). To the solution was added 1.17 g of (2S)-phosphoric acid 6-amino-2-[(4-amino-benzenesulfonyl)-isobutyl-amino]-hexyl ester diethyl ester (IX) (example 3, step B) and the mixture stirred for 3 h. 20 g of Amberlite XAD-2 resin was then added and the beads were left to soak for 10 min. The resin was transferred into a glass filter and washed thoroughly with distilled water (400 mL) and 200 mL of 1M NaHCO$_3$. The beads were then washed with 4×50 ml portions of MeOH then EtOAc 200 mL. The organic phase was evaporated. The residue was adsorbed onto silica gel and passed through a short silica gel column (EtOAc) to yield 2.4 g (83%) of white solid after evaporation.

NMR identical as in example 1A, step H.

Step B. Preparation (1S,5S)-{1-[5-[(4-amino-3-fluoro-benzenesulfonyl)-isobutyl-amino]-6-(diethoxy-phosphoryloxy)-hexylcarbamoyl]-2,2-diphenyl-ethyl}-carbamic acid methyl ester (XII)

The product of step A above, (1S,5S)-(1-{5-[(4-aminobenzenesulfonyl)-isobutyl-amino]-6-phosphonooxy hexylcarbamoyl}-2,2-diphenyl-ethyl)-carbamic acid methyl ester (0.555 g, 0.73 mmol) was dissolved in 5 mL MeCN. Selectfluor (0.26 g, 0.7 mmol) was added and the mixture stirred for 30 min. The mixture was purified by reverse phase preparative HPLC and lyophilized to yield 278 mg (48% yield) white solid.

$^1$H NMR identical as previous entry, see first methodology above.

Step C. Preparation (1S,5S)-(1-{5-[(4-amino-3-fluoro-benzenesulfonyl)-isobutyl-amino]-6-phosphonooxy-hexylcarbamoyl}-2,2-diphenyl-ethyl)-carbamic acid methyl ester (XIII, in this specific case is compound XI) (PL-515)

The procedure make this derivative was as described in the deprotection step for the methodology above. Yields 139 mg 70% after reverse phase HPLC.

$^1$H NMR identical as previous entry, see first methodology above.

Bioavailability of the Compounds

To assess the extent of in vivo cleavage of the phosphate group from the putative compounds, PL-100, PL-462 (based on PL-100), PL-337 and PL-515 (based on PL-337) compounds were administered per os (po) (50 mg/kg) to male Sprague-Dawley rats and their plasma concentration measured at different time intervals post-administration.

PL100 is an active ingredient (protease inhibitor) of the following formula;

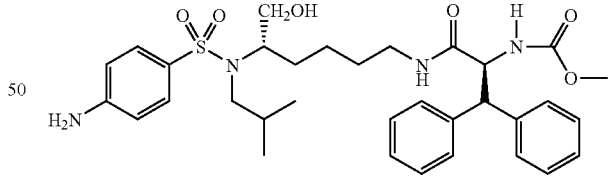

PL-337 is an active ingredient (protease inhibitor) of the following formula;

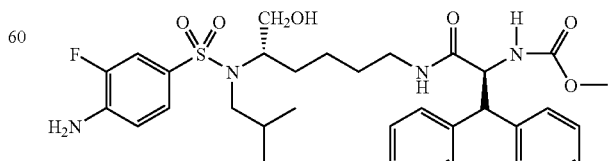

The active ingredient has been shown to be efficient against an HIV-1 aspartyl protease (U.S. Pat. No. 6,632,816). The active ingredients also present potent antiviral activity when tested on non-mutated HIV-1 viral strain (NL4.3 as the wild type virus) as well as several mutant strains.

All test articles (PL-100, PL-462, PL-337 and PL-515) were prepared in different vehicle at the final concentration of 25 mg/mL. The vehicle composition is as follows: (1) 20% ethanol; 50% propylene glycol; 0.05% w/v Tween 20 and water (Mix); (2) PBS buffer (PBS).

Test articles were administered to male Sprague-Dawley rats at a single oral dose of 50 mg/kg. Each article was tested in three rats. Blood samples (0.2-0.3 mL) were collected at the post-dose time of 10, 20, 40, 60, 120, 180 and 360 minutes. The harvested blood was centrifuged to isolate plasma. The resulting plasma was separated and stored at −70° C.

Plasma samples together with standards and quality control samples were treated to precipitate proteins, then analyzed by HPLC-MS, for the presence of PL-462, PL-100, PL-515 and PL-337.

TABLE 1

| | Compound | | | |
|---|---|---|---|---|
| | PL-462 (Ex. No. 2) | PL-100 (Ex. No. 1-F) | PL-515 (Ex. No. 6) | PL-337 (Ex. No. 6-A) |
| Vehicle | PBS | Mix | PBS | Mix |
| Number of rats | 3 | 3 | 3 | 3 |
| Dose (mg/Kg) | 50 po | 50 po | 50 po | 50 po |
| AUC (μg/hr * ml) | 0.816 ± 0.295 (PL-100, detected) | 0.675 ± 0.171 | 1.075 ± 0.625 (PL-337, detected) | 1.180 ± 0.196 |
| Cmax (nM) | 330 ± 109 | 498 ± 203 | 545 ± 215 | 681 ± 131 |
| Tmax (min) | 93 ± 60 | 40 ± 16 | 87 ± 60 | 60 ± 15 |

50 mg/Kg PL-462 = 43 mg/Kg PL-100
50 mg/Kg PL-515 = 43 mg/Kg PL-337

The results demonstrate that PL-462 and PL-515 compounds may be delivered orally in aqueous solutions. None of the PL-462 and PL-515 compounds, delivered as aqueous solutions, are detected in the blood samples, which suggests rapid metabolism to PL-100 and PL-337 the parent drugs.

Aqueous dosing of PL-462 and PL-515 solutions showed equivalent to slightly superior delivery of PL-100 and PL-337 compared to non-aqueous formulations of PL-100 and PL-337.

Based on these results, all the phosphorylated compounds described in the present invention will demonstrate similar pharmacokinetic properties.

Partition coefficient (Log P) of selected compounds and the corresponding HIV protease inhibitors (drug) are as follow:

TABLE 2

| Compounds | LogP | Corresponding drugs | LogP |
|---|---|---|---|
| PL-461 (or PL-462) | −1.2 | PL-100 | 3.6 |
| PL-515 | −0.75 | PL-337 | 3.8 |

The Log P were measured in a standard fashion by dissolving 1 mg of compound in 0.8 mL of each octanol and phosphate buffer pH 7.4 (0.04 M $KHPO_4$). The concentration of the compounds in the phases was detected by LC-MS. This test demonstrates the solubility of the compounds at physiological pH. The Log P obtained show that the compounds are highly soluble as compare to the corresponding drugs.

The numbers of the compounds listed in Table 3 (Ex. No.) corresponds to the example numbers presented above.

TABLE 3

Structures of lysine based compounds in accordance with the present invention

I

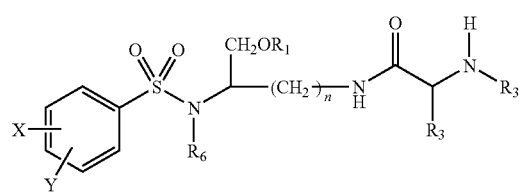

| Ex. No (PL-#) | X | Y | n | $R_1$ | $R_2$ | $R_3$ | $R_6$ | X'/Y' | D, L, DL R, S, RS |
|---|---|---|---|---|---|---|---|---|---|
| 1 (PL-461) | 4-$NH_2$ | H | 4 | $(HO)_2P(O)$ | $(C_6H_5)_2CH$ | $CH_3O$—CO | iso-butyl | H/H | S, S |
| 2 (PL-462) | 4-$NH_2$ | H | 4 | $(NaO)_2P(O)$ | $(C_6H_5)_2CH$ | $CH_3O$—CO | iso-butyl | H/H | S, S |
| 3 (PL-507) | 4-$NH_2$ | H | 4 | $(HO)_2P(O)$ | Naphthyl-2-$CH_2$ | $CH_3O$—CO | iso-butyl | H/H | S, S |
| 4 (PL-498) | 4-$NH_2$ | H | 4 | $(HO)_2P(O)$ | Naphthyl-1-$CH_2$ | 4-morpholine-CO | iso-butyl | H/H | S, S |
| 5 (PL-504) | 4-$NH_2$ | H | 4 | $(HO)_2P(O)$ | $(C_6H_5)_2CH$ | $CH_3CO$ | iso-butyl | H/H | S, S |
| 6 (PL-515) | 4-$NH_2$ | 3-F | 4 | $(HO)_2P(O)$ | $(C_6H_5)_2CH$ | $CH_3O$—CO | iso-butyl | H/H | S, S |

We claim:
1. A process for synthesizing a compound of formula IIIA:

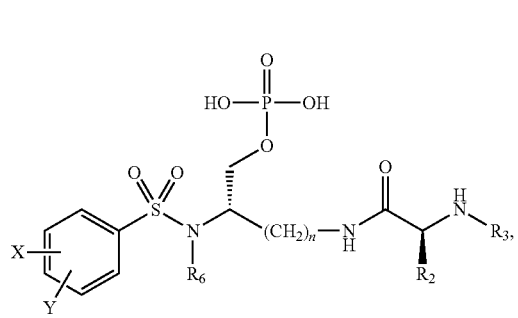

the process comprising the step of acylating a compound of formula XIV:

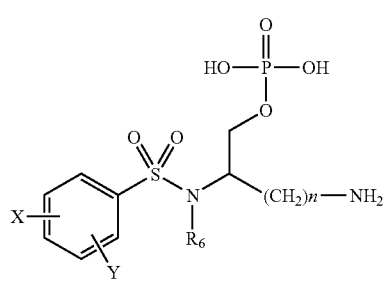

with a reactive amino acid having structure:

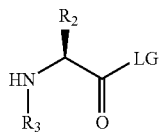

wherein LG represents a leaving group and
wherein n is 3 or 4,
wherein X and Y, the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —CF$_3$, —OCF$_3$, —CN, —NO$_2$, —NR$_4$R$_5$, —NH-COR$_4$, —OR$_4$, —SR$_4$, —COOR$_4$, —COR$_4$, and —CH$_2$OH or X and Y together define an alkylenedioxy group selected from the group consisting of a methylenedioxy group of formula —OCH$_2$O— and an ethylenedioxy group of formula —OCH$_2$CH$_2$O—,
wherein R$_3$ is selected from the group consisting of H, a straight alkyl group of 1 to 6 carbon atoms, a branched alkyl group of 3 to 6 carbon atoms, a cycloalkyl group of 3 to 6 carbon atoms, and a group of formula R$_{3,4}$—CO—, wherein R$_{3,4}$ is selected from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part thereof and 1 to 3 carbon atoms in the alkyl part thereof, an alkyloxy group of 1 to 6 carbon atoms, tetrahydro-3-furanyloxy, —CH$_2$OH, —CF$_3$, —CH$_2$CF$_3$, —CH$_2$CH$_2$CF$_3$, pyrrolidinyl, piperidinyl, 4-morpholinyl, CH$_3$O$_2$C—, CH$_3$O$_2$CCH$_2$—, Acetyl-OCH$_2$CH$_2$—, HO$_2$CCH$_2$—, 3-hydroxyphenyl, 4-hydroxyphenyl, 4-CH$_3$OC$_6$H$_4$CH$_2$—, CH$_3$NH—, (CH$_3$)$_2$N—, (CH$_3$CH$_2$)$_2$N—, (CH$_3$CH$_2$CH$_2$)$_2$N—, HOCH$_2$CH$_2$NH—, CH$_3$OCH$_2$O—, CH$_3$OCH$_2$CH$_2$O—, C$_6$H$_5$CH$_2$O—, 2-pyrrolyl, 2-pyridyl, 3-pyridyl, 4-pyridyl, 2-pyrazinyl, 2-quinolyl, 3-quinolyl, 4-quinolyl, 1-isoquinolyl, 3-isoquinolyl, 2-quinoxalinyl, a phenyl group of formula:

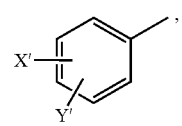

a picolyl group selected from the group consisting of

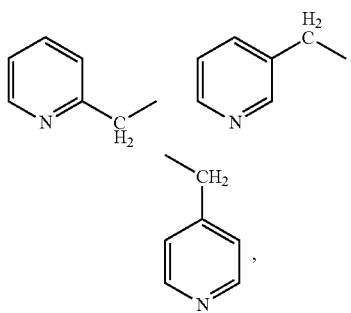

a picolyloxy group selected from the group consisting of

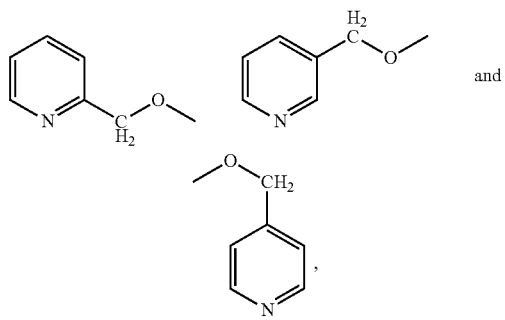

a substituted pyridyl group selected from the group consisting of

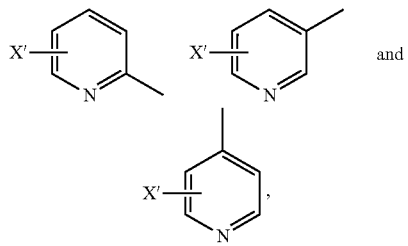

and a group of formula:

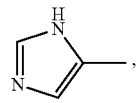

wherein R$_2$ is selected from the group consisting of a diphenylmethyl group of formula IV:

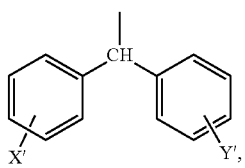

a naphthyl-1-CH$_2$— group of formula V:

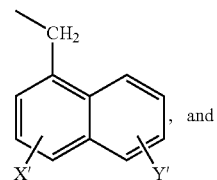

a naphthyl-2-CH$_2$— group of formula VI:

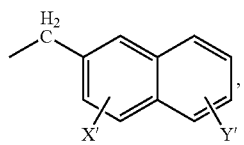

wherein X' and Y', the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —CF$_3$, —NO$_2$, —NR$_4$R$_5$, —NHCOR$_4$, —OR$_4$, —SR$_4$, —COOR$_4$, —COR$_4$ and —CH$_2$OH, wherein R$_4$ and R$_5$, the same or different, are selected from the group consisting of H, a straight alkyl group of 1 to 6 carbon atoms, a branched alkyl group of 3 to 6 carbon atoms, a cycloalkyl group of 3 to 6 carbon atoms, and tert-butoxycarbonyl, and wherein R$_6$ is selected from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof.

2. The process of claim 1, wherein the acylating step comprises:
   a. increasing the alkalinity of an aqueous solution comprising the compound of formula XIV up to pH 7 to pH 10,
   b. adding a solution comprising the reactive amino acid in a dipolar aprotic solvent and allowing reaction between the compound of formula XIV and the reactive amino acid by agitation for a period of about 1 to about 24 hours at a temperature of about 0° C. to about 40° C., and
   c. extracting the compound of formula IIIA from an aqueous phase comprising a compound of formula IIIA with a suitable solvent.

3. The process of claim 2, wherein the aqueous phase is acidified before being extracted with the solvent.

4. The process of claim 2, wherein said suitable solvent is evaporated.

5. The process of claim 3, further comprising recovering compound of formula III:

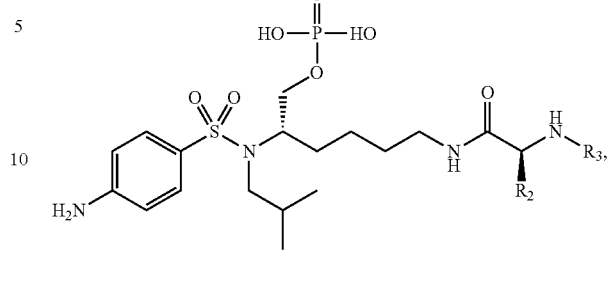

wherein R$_2$ and R$_3$ are as defined in claim 1.

6. The process of claim 1, wherein n is 4.

7. The process of claim 4, wherein X and Y, the same or different, are selected from the group consisting of methyl, ethyl, H, F, Cl, Br, I and —NR$_4$R$_5$.

8. The process of claim 7, wherein X and Y, the same or different, are selected from the group consisting of H, F and NH$_2$.

9. The process of claim 8, wherein X is NH$_2$ and Y is H or F.

10. The process of claim 9, wherein X is 4-NH$_2$.

11. The process of claim 9, wherein Y is 3-F.

12. The process of claim 1, wherein R$_6$ is selected from the group consisting of a straight alkyl group of 1 to 6 carbon atoms and a branched alkyl group of 3 to 6 carbon atoms.

13. The process of claim 12, wherein R$_6$ is iso-butyl.

14. The process of claim 1, wherein the reactive amino acid has structure:

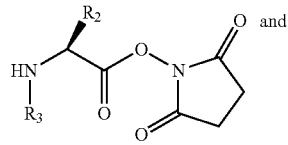

wherein R$_2$ and R$_3$ are as defined in claim 1.

15. A process for synthesizing a compound of formula IIIB:

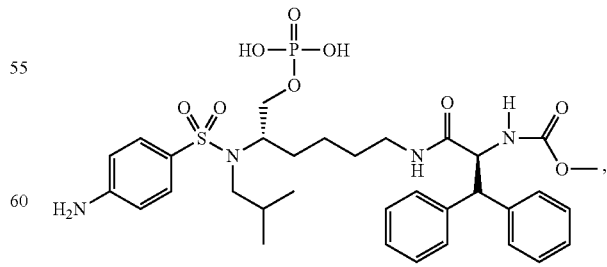

the process comprise the step of acylating a compound of formula XIX:

XIX

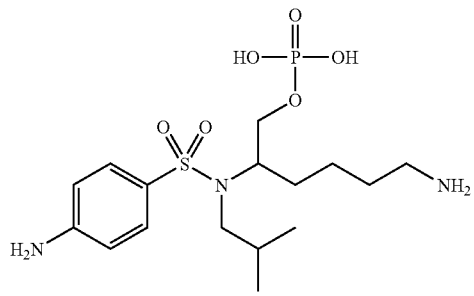

with a reactive amino acid of formula:

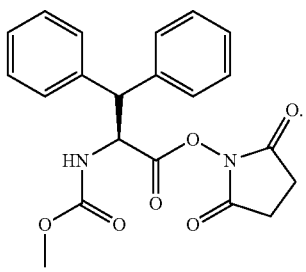

16. The process of claim 15, wherein the acylating step comprises:
   a. increasing the alkalinity of an aqueous solution comprising the compound of formula XIV up to pH 7 to pH 10,
   b. adding a solution comprising the reactive amino acid in a dipolar aprotic solvent and allowing reaction between the PL-461 compound and the reactive amino acid by agitation for a period of about 1 to about 24 hours, and
   c. extracting the compound of formula IIIB from an aqueous phase comprising the IIIB compound with a suitable solvent.

17. The process of claim 16, wherein the aqueous phase is acidified before being extracted with said suitable solvent.

18. The process of claim 16, wherein the solvent is evaporated.

19. A process for the preparation of compound IIIB:

IIIB

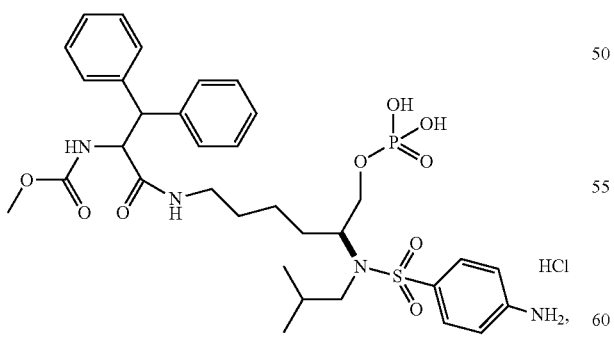

said process comprising the steps of
a) phosphorylating a compound of formula XVII:

XVII

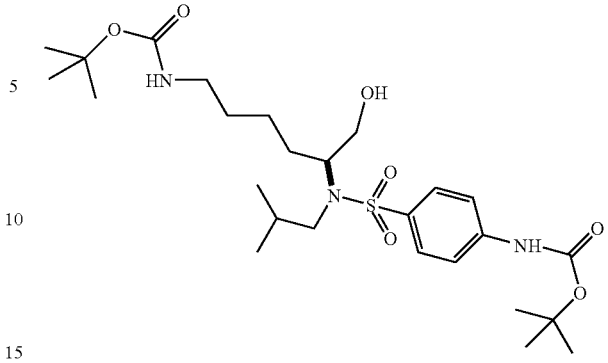

in the presence of an organic base in a dipolar aprotic solvent,
b) hydrolysizing the compound obtained in a) in the presence of concentrated hydrochloric acid to provide a water soluble hydrochloric salt of phosphoric acid mono ester, and
c) acylating an aqueous solution of b) with a suitable reactive amino acid of the formula:

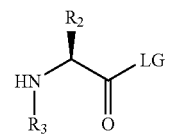

to provide the phosphate mono ester of formula IIIB:

IIIB

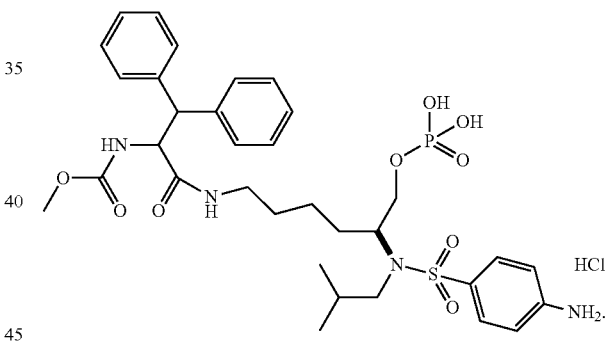

20. The process of claim 19, wherein the dipolar aprotic solvent is methyl iso-butyl ketone or acetone.

21. The process of claim 20, wherein said suitable reactive amino acid is a compound of formula:

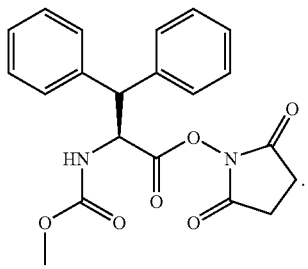

* * * * *